(12) United States Patent
Gopalsamy et al.

(10) Patent No.: US 6,586,187 B1
(45) Date of Patent: Jul. 1, 2003

(54) METHODS FOR SOLID PHASE COMBINATORIAL SYNTHESIS OF INTEGRIN INHIBITORS

(75) Inventors: Ariamala Gopalsamy, Mahwah, NJ (US); Hui Y. Yang, New City, NY (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 09/548,697

(22) Filed: Apr. 13, 2000

Related U.S. Application Data

(60) Provisional application No. 60/240,952, filed on Apr. 14, 1999, now abandoned.

(51) Int. Cl.[7] ................ G01N 33/53; C07K 1/06; C07D 295/00

(52) U.S. Cl. .............. 435/7.1; 435/4; 435/DIG. 22; 435/DIG. 34; 435/DIG. 40; 514/252.12; 514/253.01; 530/333; 530/334; 530/335; 544/295; 544/358; 544/340; 544/400

(58) Field of Search ................ 544/295, 358, 544/360, 400; 514/252.12, 253.01; 435/4, 7.1, DIG. 22, DIG. 34, DIG. 40; 530/333–335

(56) References Cited

U.S. PATENT DOCUMENTS 5,681,820 A    10/1997    Ruminski

FOREIGN PATENT DOCUMENTS

| WO | WO9532710 | 12/1995 |
|---|---|---|
| WO | WO9708145 | 3/1997 |
| WO | WO9733887 | 9/1997 |

OTHER PUBLICATIONS

Hermkens, P.H. et al., Tetrahedron, 52, 4527–4554 (1996).
Choi et al., J. Vasc. Surgery, 19, 125–134 (1994).
Matsumo et al., Circulation, 90, 2203–2206 (1994).
White et al., Current Biology, 596–599 (1993).
Davies et al., J. Cell. Biol., 109, 1817–1826 (1989).
Helfrich et al., J. Bone Mineral Res., 7, 335–343 (1992).
Horton et al., Exp. Cell Res., 195, 368–375 (1991).
Fisher et al., Endocrinology, 132, 1411–1413 (1993).
Engleman et al., J. Clin. Invest., 99, 2284–2292 (1997).
Borman, S. Chem. & Engineering News, 75(8), 43–63 (1997).
Corbett, J.W. et al., Bioorganic & Med. Chem. Lett., 7, 1371–1376 (1997).

*Primary Examiner*—Bennett Celsa
(74) *Attorney, Agent, or Firm*—Rebecca R. Barrett; Kimberly R. Hild

(57) ABSTRACT

Compounds of the formula

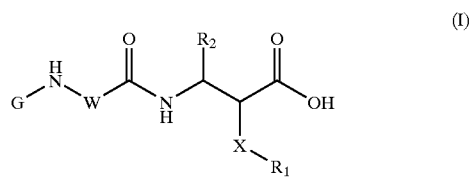

are useful in the treatment of various disorders including, but not limited to, cancer (tumor metathesis, tumorgenesis/tumor growth), angiogenesis (as in cancer, diabetic retinopathy, rheumatoid arthritis), restenosis (following balloon angioplasty or stent implantation), inflammation (as in rheumatoid arthritis, psoriasis), bone diseases (osteopenia induced by bone metastases, immobilization and glucocortocoid treatment, periodontal disease, hyperparathyroidism and rheumatoid arthritis), and as antiviral agents. Novel method of making compounds of formula I are also provided.

12 Claims, No Drawings

METHODS FOR SOLID PHASE COMBINATORIAL SYNTHESIS OF INTEGRIN INHIBITORS

This application claims the benefit of U.S. Ser. No. 09/291,470, which was converted to a Provisional Application No. 60/240,952, filed Apr. 14, 1999 now abandoned.

FIELD OF INVENTION

The present invention relates to integrin inhibitors useful for their ability to antagonize/block biological processes mediated by $\alpha v \beta 3$ and related integrin receptors, to combinatorial and solid phase methods for preparing libraries of compounds, and utilization of libraries of the compounds for drug discovery. The present invention further provides pharmaceutical compositions for administration to mammals, including man, and methods for their use in the treatment of various disorders including, but not limited to, cancer (tumor metathesis, tumorgenesis/tumor growth), angiogenesis (as in cancer, diabetic retinopathy, rheumatoid arthritis), restenosis (following balloon angioplasty or stent implantation), inflammation (as in rheumatoid arthritis, psoriasis), bone diseases (osteopenia induced by bone metastases, immobilization and glucocortocoid treatment, periodontal disease, hyperparathyroidism and rheumatoid arthritis), and as antiviral agents.

BACKGROUND OF INVENTION

The solid phase synthesis of non-peptidic small organic molecules is a rapidly evolving area of research with applications in the preparation of combinatorial libraries. While the solid phase synthesis of peptides is well established, the solid phase synthesis of non-peptidic small organic molecules is still evolving (Hermkens, P. H. H.; Ottenheijm, H. C. J.; Rees, D. Tetrahedron 1996, 52, 4527–4554). In particular, methods for solid phase synthesis of molecules of biological significance is of importance to drug discovery and is an active area of research.

The integrin $\alpha_v \beta_3$ has been shown to mediate the invasion of cancerous melanoma cells into healthy tissue and to protect these cells against natural cell death cycle (apoptosis). Vitronectin receptor($\alpha_v \beta_3$) antagonists have been shown to inhibit the growth of various solid tumors of human origin. More recently, $\alpha_v \beta_3$ has been shown to be involved in liver metastasis. Although angiogenesis is an important and natural process in growth and wound healing, it is now appreciated that a variety of clinically relevant conditions are pathologically related to these processes, and that the integrin $\alpha_v \beta_3$ is involved. For example, $\alpha_v \beta_3$ was shown to be expressed on human wound tissue but not on normal skin and is preferentially expressed on angiogenic blood vessels, such as those feeding a growing/invading tumor. It has also been shown that antagonists of $\alpha_v \beta_3$ promote tumor regression by inducing apoptosis of the tumor cells. This process of neovascularization (new blood vessel growth, angiogenesis), which is critical for tumor growth and metastasis, is also an important event in occular tissue, leading to diabetic retinopathy, glaucoma and blindness and in joints, promoting rheumatoid arthritis.

$\alpha_v \beta_3$ has been shown to play a pivotal role in the proliferation and migration of smooth muscle and vascular endothetial cells, a pathological process leading to restenosis after balloon angioplastly (Choi et al., J. Vasc. Surgery, 1994, 19, 125–134; Matsumo et al., Circulation, 1994, 90, 2203–2206). At least one type of virus (adenovirus) has been shown to utilize ($\alpha_v \beta_3$ for entering host cells (White et al., Current Biology, 1993, 596–599).

Various bone diseases involve bone resorption-the dissolution of bone matter, which is mediated by only one known class of cells, the osteoclasts. When activated for resorption, these motile cells initially bind to bone, a process well known to be mediated by asps (Davies et al., J. Cell. Biol., 1989, 109, 1817–1826; Helfrich et al., J Bone Mineral Res., 1992, 7, 335–343). It is also well known that blockade of $\alpha_v \beta_3$ with antibodies or RGD containing peptides block osteoclast cell adhesion and bone resorption in vitro (Horton et al., Exp. Cell Res. 1991, 195, 368–375) and that echistatin, an RGD containing protein, inhibits bone resorption in vivo (Fisher et al., Endocrinology, 1993, 132, 1411–1413). More recently, an RGD peptidomimetic has likewise been shown to inhibit osteoclats in vitro and, by i.v. administration prevents osteoporosis (Engleman et al., J. Clin. Invest., 1997, 99, 2284–2292). Numerous patents/applications have claimed various non-peptide $\alpha_v \beta_3$ inhibitors for some or all of the above applications (e.g.WO 95/32710, WO 97/08145, WO 97/33887, U.S. Pat. No. 5,681,820).

Combinatorial chemistry is becoming an important tool for drug discovery and lead optimization (Borman, S. Chemical and Engineering News 1997, 75 (8), 43–63). A combinatorial synthesis requires that at least two components of the product molecules be independently variable, so that all of the combinations of these components can be prepared. A synthesis with three independently variable components is preferable since greater diversity in structure can be produced in the resultant library. Thus to prepare a combinatorial library of integrin inhibitors with a high degree of potential diversity and wide utility for drug discovery using solid phase techniques, it is important to identify a synthesis in which three components can be independently varied.

Most of the reported integrin inhibitors are RGD mimics and they use a β-amino acid like substituted 2,3-diaminopropionic acid as the carboxylic acid terminus. While a cyclic or acyclic guanidino moiety is preferred for the basic end of the molecule, substituted ureas and amidines are used as well. The central scaffold, connecting these two pieces, itself can be varied widely. By developing a convenient route to appropriately protected fragments and a mild solid phase synthesis that incorporates all the three components in an independent fashion, it is possible to prepare combinatorial libraries of this important class of integrin inhibitors.

A solid-phase synthesis of integrin antagonist has been reported recently (Corbett, J. W.; Graciani, N. R.; Mousa, S. A.; DeGrado, W. F. Bioorganic & Med Chem Lett. 1997, 7, 1371–1376). However, this synthesis on solid phase does not provide a means of varying the substitutions on the β-amino acid of the carboxy terminus and uses the commercially available α-N-CBZ-diaminopropionic acid as the only fragment. Hence, a combinatorial library synthesized using this method has limited utility in the drug discovery process lacking structure-activity data for all the regions of the molecule that can be independently varied. It is important to optimize this region of the inhibitors since the lipophilic substitutents in this region and the linkers used to connect these substituents have a significant effect on the activity of this class of molecules.

Multiple compounds can be generated simultaneously by solid phase synthesis. The solid phase synthesis detailed in the present invention for the simultaneous generation of a library of integrin inhibitors where all three components can be varied is not known. The preparation of libraries of compounds of the present invention is useful because it provides rapid structural variation and structure-activity information.

BRIEF DESCRIPTION OF INVENTION

Accordingly, the present invention discloses a solid phase synthesis process for producing compounds represented in formula (I):

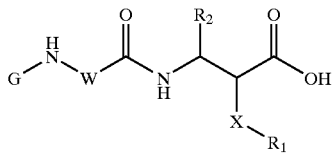

wherein:

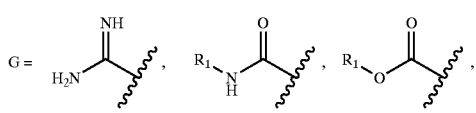

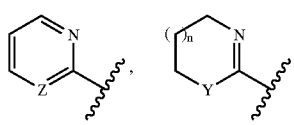

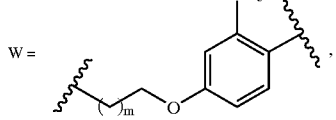

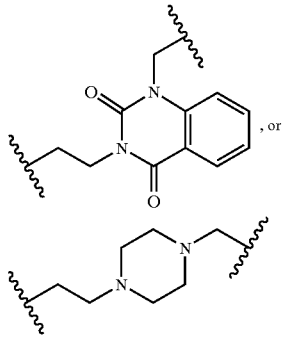

R1 and R2 independently are alkyl of 1–8 carbon atoms, alkenyl of 2–8 carbon atoms, alkynyl of 2–8 carbon atoms, cycloalkyl of 3–12 carbon atoms, aryl, aralkyl of 6 to 10 carbon atoms, heterocycloalkyl of 5–10 members consisting of carbon atoms and from 1 to 3 heteroatoms selected from N, S and O;

R3 is H, alkyl of 1–6 carbon atoms, aralkoxy of 1–6 carbon atoms;

X is NHCOO, NHCO, NHCONH, NHSO$_2$;

Y is CH$_2$, NH;

Z is CH, N, S m is 0–4; and n is 0–3; or pharmaceutical salts thereof.

In some aspects of the invention G may preferably be pyrimidinyl, guanidine, pyridyl-urea, benzyl-urea, azepinyl, imidazolinyl or tetrahydropyrimidinyl.

In other aspects of the invention R1 may be methyl, ethyl, n-propyl, i-propyl, allyl, homoallyl, propargyl, pentyl, n-hexyl, octyl, neopentyl, trichloroethyl, n-butyl, i-butyl, butynyl, phenyl, methylphenyl, dimethylphenyl, halophenyl, methoxyphenyl, acetylphenyl, biphenyl, naphthyl, benzyl, phenethyl, cyclohexyl, cyclohexylmethyl, trimethylcyclopropyl, phenylcyclopropyl, adamantyl, adamantylmethyl, cinnamic, pyridyl, or dimethylfuranyl.

In some preferred aspects of the present invention are provided compounds of Formula (I) wherein G, W, R1, R2, R3, X, Y, Z, m and n are defined above, with the proviso that when W is

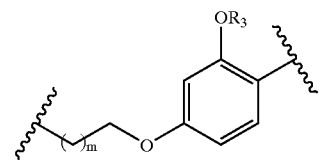

and R3 is H, then G is not:

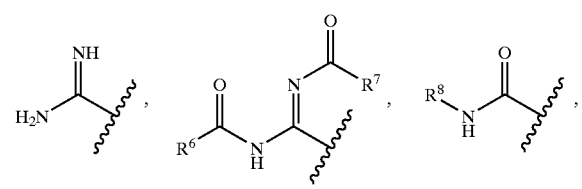

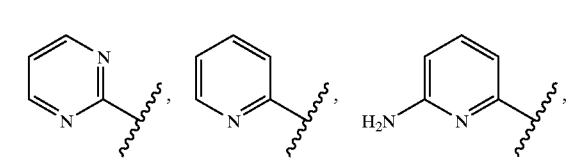

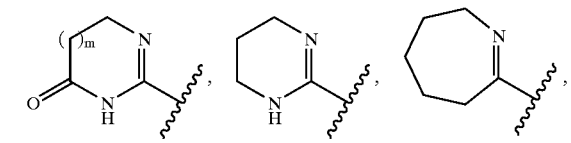

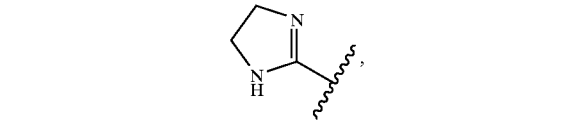

In still other preferred embodiments of the present invention G is

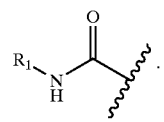

In other embodiment of the present invention it is preferred that W is

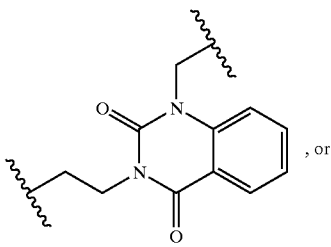

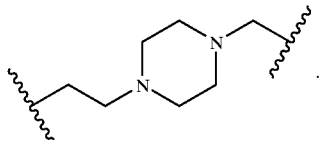

In yet other embodments of the present invention G is

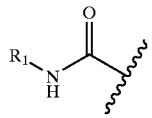

and W is

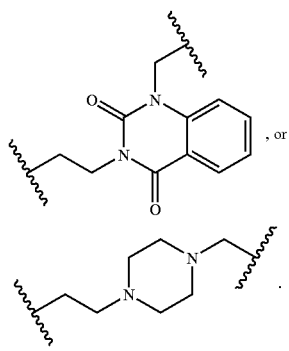

"Alkyl", whether used alone or as part of a group such as "alkoxy", means a branched or straight chain having from 1 to 10 carbon atoms. Exemplary alkyl groups include methyl, ethyl, propyl, isopropyl, butyl, isobutyl, t-butyl, pentyl and hexyl. Lower alkyl refers to alkyl having from 1 to 6 carbon atoms. In some preferred embodiments of the present invention alkyl is from 1 to 8 carbon atoms. Alkyl groups may be substituted with one or more substituents selected from halogen, lower alkyl, lower alkoxy, lower alkylthio, amino, nitro, cyano, carboxy, alkylamino, perhaloalkyl, hydroxy, oxy, phenyl, phenylalkyl, or naphthyl.

"Cycloalkyl" as used herein refers to mono or polycyclic alkyl group of 3–12 carbon atoms. Exemplary cycloalkyl groups include cyclopropyl, cyclohexyl and adamantyl. Cycloalkyl groups may be substituted. One preferred substitution is phenyl.

"Aryl" whether used alone or as part of a group such as "aralkyl", means mono or bicyclic aromatic ring having from 5 to 10 carbon atoms. Exemplary aryl groups include phenyl and naphthyl. The aryl may be substituted with one or more substituents. Substituents include halogen, lower alkyl, lower alkoxy, lower alkylthio, amino, nitro, cyano, carboxy, carboxyalkyl, alkanoyl, alkylamino, perhaloalkyl, hydroxy, oxy, phenyl, phenylalkyl, or naphthyl. One preferred aryl group is phenyl which may be denoted as Ph in some instances.

"Heterocycloalkyl" whether used alone or as part of a group such as "heterocycloalkyl-alkyl" means a stable 5 to 10 membered mono or bicyclic ring of carbon atoms and from 1 to 3 heteroatoms selected from N, O and S. Exemplary heterocycloalkyls include pyrazinyl, pyrazolyl, tetrazolyl, furanyl, thienyl, pyridyl, imidazolyl, pyrimidinyl, tetrahydropyrimidinyl, isoxazolyl, thiazolyl, isothiazolyl, quinolinyl, indolyl, isoquinolinyl, oxazolyl and oxadiazolyl. Preferred heterocycloalkyl groups include pyrimidinyl, tetrahydropyrimidinyl, pyridyl, azepinyl, and imidazolyl. Most preferred heterocycloalkyls include pyridin-2yl, and tetrahydropyrimidine. The heterocycloalkyl may also be substituted with one or more substituents. Substituents include halogen, lower alkyl, lower alkoxy, lower alkylthio, amino, nitro, cyano, carboxy, carboxyalkyl, alkanoyl, alkylamino, perhaloalkyl, hydroxy, oxy, phenyl, phenylalkyl or naphthyl. Preferred substituents include amino and oxy. Preferred substituted heterocyloalkyls include 6 aminopyridin-2yl and tetrahydropyrimid-4-one.

"Aralkyl" means an aryl-alkyl group in which the aryl and alkyl are as previously described. Exemplary aralkyl groups include benzyl and phenethyl. Used in this context, the alkyl group may include one or more double bonds.

"Heterocycloalkyl-alkyl" means an heterocycloalkyl-alkyl group in which the heterocycloalkyl and alkyl are as previously described. Used in this context the alkyl group may include one or more double bonds. Exemplary heterocycloalkyl-alkyls include pyridylmethyl, pyridylethyl, thienylethyl, thienylmethyl, indolylmethyl, and furylmethyl.

"Alkoxy" means an alkyl-O group in which the alkyl group is as previously described. Exemplary alkoxy groups include methoxy, ethoxy, n-propoxy, i-propoxy, n-butoxy, and t-butoxy.

"Aralkoxy" means an aryl-alkoxy group in which aryl and alkoxy are as previously described.

"Halogen" includes fluorine, chlorine, iodine and bromine.

"Prodrug", as used herein means a compound which is convertible in vivo by metabolic means (e.g. by hydrolysis) to a compound of Formula I.

Compounds of the present invention include all crystalline forms, pharmaceutically acceptable salts, enantiomers, racemic mixtures, and diasteromeric mixtures thereof.

Some preferred compounds of the present invention include:

2-benzyloxycarbonylamino-3-(2-{4-[2-(3-benzylureido)-ethyl]-piperazin-1-yl}acetylamino)-propionic acid; and
2-benzyloxycarbonylamino-3-(2-{4-[2-(3-benzylureido)-ethyl]-2,4-dioxo-3,4-dihydro-2H-quinazolin-1-yl}acetylamino)-propionic acid and pharmaceutically acceptable salts thereof Compounds of the present invention may be prepared in accordance certain solid phase methodology. In one aspect of the present invention, compounds of Formula (I) where

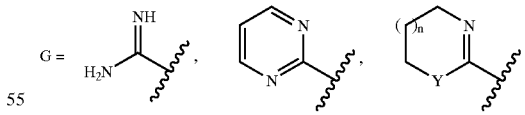

may be prepared in accordance with the steps of:

a) attaching a β-amino acid of the formula

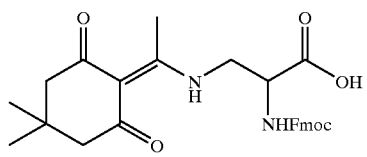

to a solid support P to produce a compound of formula (1)

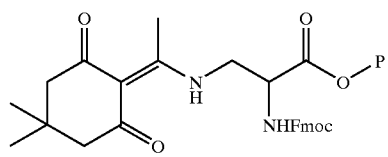
(1)

wherein P is preferably a polystyrene resin cross-linked with divinylbenzene and functionalized with a linker such as a hydroxymethylphenoxy group, which is more preferably Wang's resin:

b) deblocking the fluorenylmethyloxy carbonyl group of said compound of formula (1) with piperidine to produce a compound of formula (2);

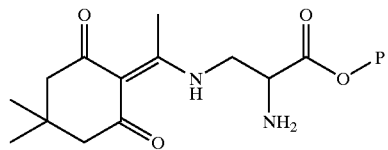
(2)

c) acylating compound of formula (2) with a chemical species selected from chloroformates, isocyanates, sulfonyl chlorides, carboxylic acid chlorides or carboxylic acids to produce a compound of formula (3)

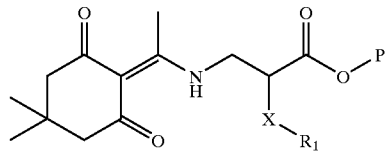
(3)

wherein X and $R_1$ are as defined above;

d) deblocking the 4,4-dimethyl-2,6-dioxocylohex-1-ylideneethyl protecting group of said compound of formula (3) with hydrazine to produce a compound of formula (4);

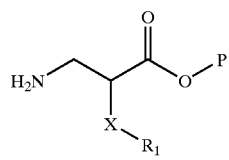
(4)

e) reacting said compound of formula (4) with a Fmoc protected amino carboxylic acid of formula (5)

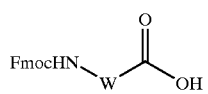
(5)

wherein W is as defined above, to produce a compound of formula (6);

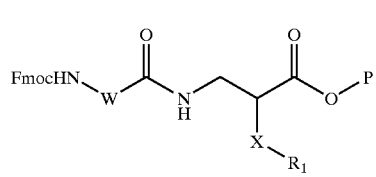
(6)

f) deblocking the fluorenylmethyloxy carbonyl group of said compound of formula (6) with piperidine to produce a compound of formula (7);

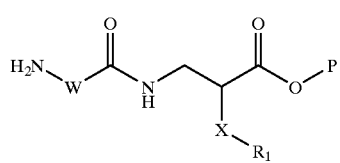
(7)

g) reacting said compound of formula (7) with guanidilation reagents of formula (8) or (9) or (10) or amidation reagent of formula (11)

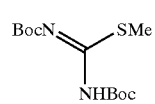
(8)

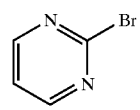
(9)

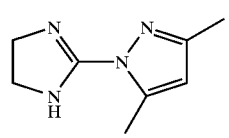
(10)

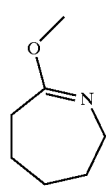
(11)

to produce a compound of formula (12)

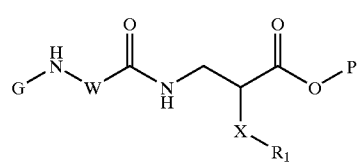
(12)

-continued wherein

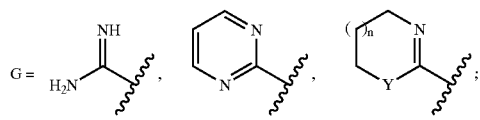

and h) reacting said compound of formula (12) with a cleaving reagent like trifluoroacetic acid to produce a compound of formula (I)

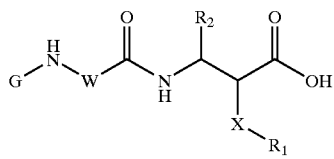
(I)

wherein $R_1$, X, W and G are as defined above.

Also in accordance with the present invention, where

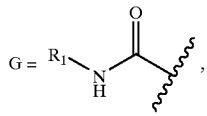

compounds of Formula I may be prepared in accordance with steps a) through f) to produce compound of formula (7).

This aspect of the methods of the invention further comprises the steps of:

i) reacting said compound of formula (7) with isocyanates or with p-nitrophenyl chloroformate, followed by amine to produce a compound of formula (12)

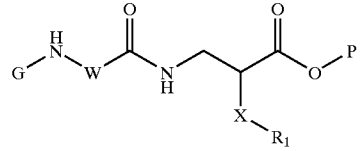
(12)

wherein

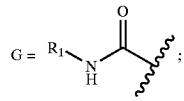

and i) reacting said compound of formula (12) with a cleaving reagent like trifluoroacetic acid to produce a compound of formula (I)

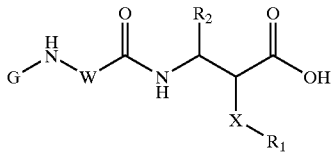
(I)

wherein $R_1$, X, W and G are as defined above.

The compounds of the present invention may be prepared according to the general process outlined in Scheme I.

Scheme I

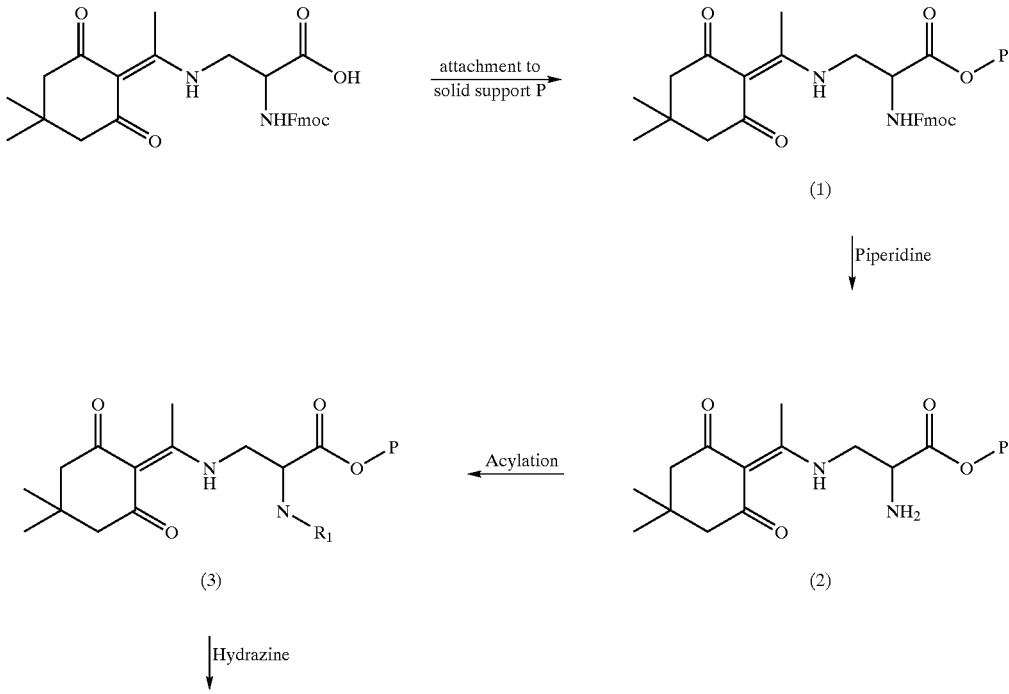

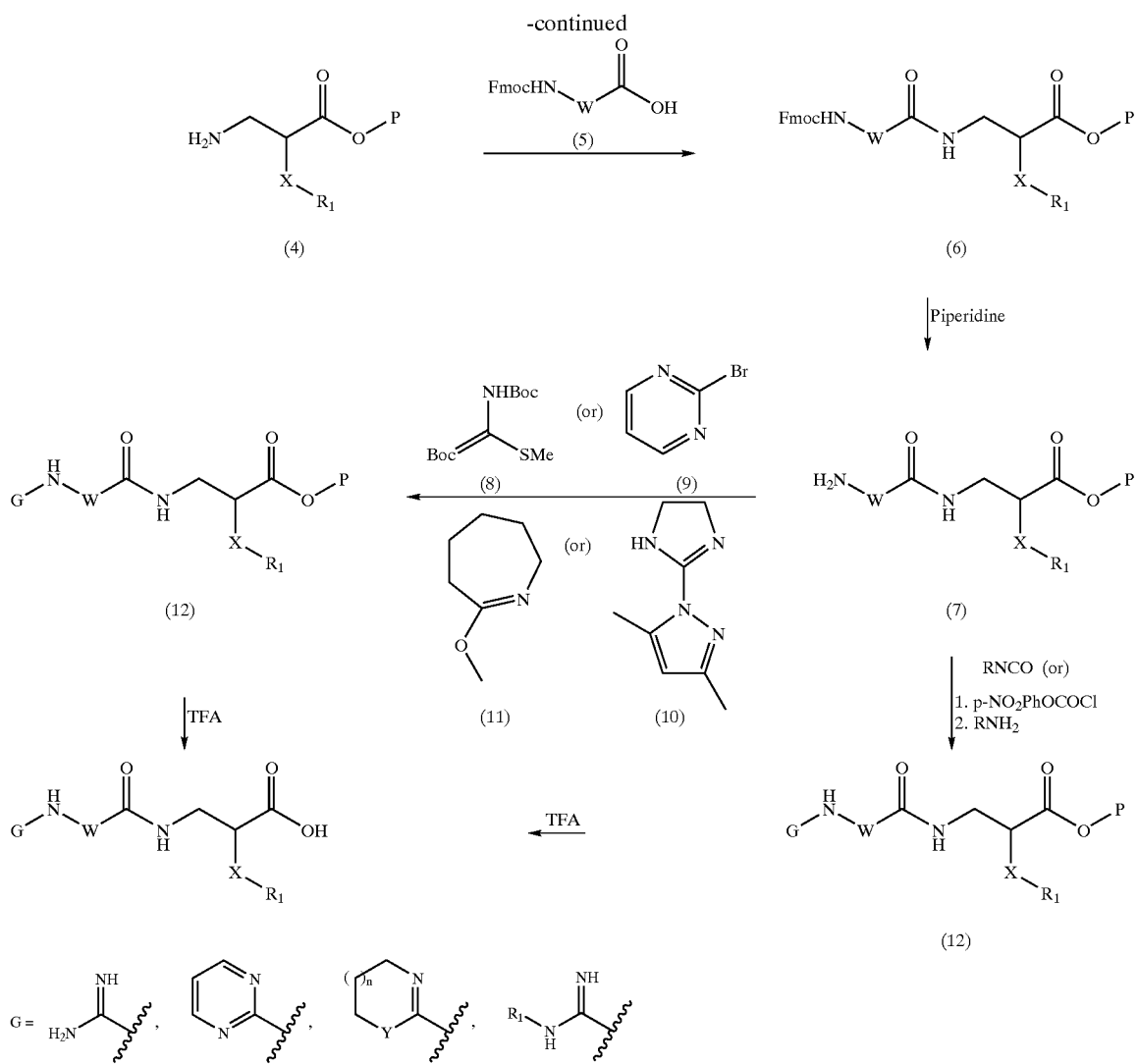

Thus, the orthogonally protected 2,3-diaminopropionic acid is attached to a solid support P, which is preferably a resin of polystyrene cross-linked with divinylbenzene and with a linker such as 4-hydroxymethylphenoxy, most preferably Wang's resin as described below, in the presence of a coupling reagent such as 2-(1H-benzotriazole-1-yl)-1,1,3,3-tetramethyluronium hexafluorophosphate (HBTU)/N-hydroxybenzotriazole (HOBT) to produce a compound of formula (1). The compound of formula (1) is deprotected using 20% piperidine in DMF to yield a compound of formula (2), which provides the first handle for diversification.

A compound of formula (2) is reacted with either chloroformates or isocyantes or carboxylic acid chlorides or sulfonyl chlorides in a solvent like dichloromethane or tetrahydrofuran to yield a compound of formula (3). Alternatively, in the case of amide formation, a carboxylic acid is coupled directly with the compound of formula (2) in the presence of a coupling reagent like 1,3-diisopropylcarbodiimide (DIC) to produce the compound of formula (3). A compound of formula (3) is treated with 2% hydrazine to deprotect the (4,4-dimethyl-2,6-dioxocyclohex-1-ylidene)ethyl (dde) protecting group to yield a compound of formula (4), which provides a second handle for diversification. A compound of formula (4) is reacted with a Fmoc protected amino carboxylic acid of formula (5) in the presence of a coupling reagent like DIC to produce the compound of formula (6). The compound of formula (6) is deprotected using 20% piperidine in DMF to yield a compound of formula (7), which provides the third handle for diversification. The compound of formula (7) is reacted with N,N-bis-Boc-S-ethylthiourea or 2-(3,5-dimethylpyrazolyl)-4,5-dihydroimidazole or 2-bromopyrimidine or 1-methoxy-2-azacylohept-1-ene to give a compound of formula (12). Alternatively, the compound of formula (7) is reacted with p-nitrophenyl chloroformate and the resulting carbamate was reacted with amines to give ureas of formula (12).

The compounds of the present invention are integrin inhibitors useful for their ability to antagonize biological processes mediated by αvβ3 and related integrin receptors including, but not limited to, cancer (tumor metastatis, tumorgensis, tumor growth), angiogenesis (as in cancer, diabetic retinopathy, rheumatoid arthritis), restenosis (following balloon angioplasty or stent implantation), inflammation (as in rheumatoid arthritis, psoriasis), bone diseases (osteopenia induced by bone metastases, immobilization and glucocortocoid treatment, periodontal disease, hyperparathyroidism and rheumatoid arthritis), and as antiviral agents. The effect of the compounds to inhibit integrin is determined by standard pharmacological tests.

Vitronectin Receptor ($\alpha_v\beta_3$) Binding Assay

The purpose of this assay is to measure the effect of various compounds on the $\alpha_v\beta_3$-ligand interaction.

Reagents

Plasma Membrane Isolation: 15 confluent $T_{150}$ flasks of 512P5 cells ($\alpha_v\beta_3$ -over expressing cell line) are washed 2× with Dulbecco's phosphate buffered saline (D-PBS) without calcium or magnesium, pH 7.1. Cells are harvested with 10 mL of trypsin/EDTA and collected by centrifugation. The cell pellet is washed 2× with 0.5 mg/mL of soybean trypsin inhibitor, and resuspended at 10% weight/volume in homogenization buffer (25 mM Tris-HCl, pH=7.4; 250 mM sucrose). The cell suspension is homogenized with 2×30 (seconds bursts of a Polytron homogenizer. The homogenate is centrifuged at 3000 g for 10 minutes at 4° C. The supernatant is collected, measured, and made 100 mM in NaCl and 0.2 mM in $MgSO_4$. The supernatant is centrifuged at 22,000 g for 20 minutes at 4° C., the pellet is resuspended in 7 mL of membrane buffer (25 mM Tris-HCl, pH=7.4; 100 mM NaCl; 2 mM $MgCl_2$) by 5 strokes of a Dounce homogenizer (tight pestle) and recentrifuged at 22,000 g for 20 minutes at 4° C. The pellet is resuspended in 0.5 mL/flask of membrane buffer (stock membranes) and frozen at −80° C. Prior to use, stock membranes are Dounce homogenized and diluted 2 µL to 1000 µL in membrane buffer. See References Compound Dilution: The stock compounds are dissolved in an appropriate vehicle (typically DMSO) and subsequently diluted in assay buffer composed as follows: 25 mM Tris-HCl (pH=7.4), 100 mM NaCl, 2 mM $MgCl_2$, 0.1% BSA.

Plate Preparation

Wells of Multiscreen-FB assay plates (Millipore MAFB NOB 50) are blocked with 150 mL of 0.1% polyethylenimine for 2 hours at 4° C. Following incubation the wells are aspirated and washed with isotonic saline solution.

Binding Assay

125 µL of assay buffer is added to each well. Next, 25 µL of labeled ligand is added to each well. 25 µL of unlabeled ligand is added to non-specific binding wells (NSB). 25 µL of assay buffer is added to all other wells. 2 µL of compound is added to appropriate sample wells, and 2 µL of DMSO is added to NSB and total binding (TB) wells. Finally, 25 µL of membrane is added to each well.

The plates are covered and incubated at 37° C. for 2 hours in a humidified incubator. Wells are aspirated on a Millipore vacuum manifold, and the wells are washed with 150 µL isotonic saline solution. Wells are again aspirated. The plates are then dried for 1 hour in an 80° C. vacuum drying oven. Plates are placed on a Millipore filter punch apparatus, and filters are placed in 12×75 mm polypropylene culture tubes. The samples are counted on a Packard gamma counter.

EXAMPLE

Using $^{125}$I-Echistatin (specific activity=2000 Ci/mmol) supplied by Amersham at a final concentration of 50 pM, the following parameters are routinely observed;

| | |
|---|---|
| Input | 80000 cpm |
| Total Counts | 8000 cpm |
| Non-specific binding | 200 cpm |

Analysis of Results

The individual well activity is expressed as a percentage of the specific binding; % Max, and reported as the mean±standard deviation. Dose-inhibition relationships are generated for dose (X-axis) vs. % Max (Y-axis) for active compounds using a non-linear regression computer program (PS-NONLIN), and $IC_{50}$ values with corresponding 95% confidence intervals are estimated from 50% of maximal attachment.

Reference Compounds

Various Arginine-Glycine-Aspartic Acid (RGD)-containing peptides were assessed for the ability to inhibit $a_v b_3$ binding and the corresponding $IC_{50}$ values with 95% confidence intervals were generated; peptide structures are given by the standard single letter designation for amino acids. Values obtained compared favorably with adhesion assay results.

| SEQ ID NO. | PEPTIDE | IC50 (µM) | 95% confidence interval |
|---|---|---|---|
| 7 | GPenGRGDSPCA | 0.064 | 0.038 to 0.102 |
| 1 | GRGDSP | 1.493 | 1.058 to 2.025 |
| 2 | GRGDTP | 0.490 | 0.432 to 0.556 |
| 3 | GRGDS | 0.751 | 0.690 to 0.817 |
| 4 | RGDS | 1.840 | 1.465 to 2.262 |
| 5 | GRGDNP | 0.237 | 0.144 to 0.353 |
| 9 | GdRGDSP | 0.692 | 0.507 to 0.942 |
| 6 | GRGESP | inactive at 100 µM | |

REFERENCE

1. Nesbitt, S. A. And M. A. Horton, (1992), *A nonradioactive biochemical characterization of membrane proteins using enhanced chemiluminescence*, Anal. Biochem., 206 (2), 267–72.

Osteopontin-$\alpha_v\beta_3$ Cell Attachment Assay

The purpose of this assay is to measure the effect of various compounds on the RGD-dependent attachment of cells to osteopontin mediated by the $\alpha_v\beta_3$ integrin.

Reagents

Cell Suspension Media

The cells are suspended for assay in the tissue culture media used for normal culture maintenance buffered with 25 mM HEPES (pH 7.4) without serum supplementation.

Compound Dilution Media

The stock compounds are dissolved in an appropriate vehicle (typically DMSO) and subsequently diluted in the tissue culture media used for normal culture maintenance buffered with 25 mM HEPES (pH 7.4) supplemented with 0.2% BSA (no serum); final vehicle concentration is ≦0.5%.

Plate Preparation

Human recombinant osteopontin (Structural Biology Group, W-AR) is diluted to an appropriate concentration in Dulbecco's phosphate buffered saline (D-PBS) without calcium or magnesium, pH 7.1. 100 mL of this solution is incubated in the wells of PRO-BIND assay plates (Falcon 3915) for 2 hours at 37° C. Following incubation the wells are aspirated and washed once with D-PBS; plates can either be used immediately or stored for up to 1 week at 4° C. Prior to assay, the wells are blocked with 1% bovine serum albumin (BSA) in cell suspension media for 1 hour at 37° C. Following the blocking period, wells are aspirated and washed once with D-PBS.

Cell Suspension $\alpha_v\beta_3$-expressing cell lines are maintained by standard tissue culture techniques. For assay, the cell monolayer is washed three times with D-PBS, and the cells are harvested with 0.05% trypsin/0.53 mM EDTA (GIBCO). The cells are pelleted by low-speed centrifugation and washed three times with 0.5 mg/mL trypsin inhibitor in D-PBS (Sigma). The final cell pellet is resuspended in cell suspension media at a concentration of $10^6$ cells/mL.

Attachment Assay

Incubation 100 mL of diluted test compound is added to osteopontin-coated wells (in triplicate) followed by 100 mL of cell suspension; background cell attachment is determined in uncoated wells. The plate is incubated at 25° C. in a humidified air atmosphere for 1.5 hours. Following the incubation period, the wells are gently aspirated and washed once with D-PBS.

Cell Number Detection

The number of cells attached is determined by an MTT dye conversion assay (Promega) according to the manufacturer's instructions. Briefly, MTT dye is diluted in cell suspension media (15:85) and 100 mL is added to each well. The assay plates are incubated for 4 hours at 37° C. in a humidified 5% $CO_2$/95% air atmosphere, followed by the addition of 100 mL stopping/solubilization solution. The assay plates are covered and incubated at 37+ C. in a humidified air atmosphere overnight. After the solubilization period, the optical density of the wells is measured at a test wavelength of 570 nM with a reference measurement taken simultaneously at 630 nM.

Analysis of Results

The individual well optical density is expressed as a percentage of the maximal attachment (% Max) wells minus background attachment, and reported as the mean±standard deviation. Dose-inhibition relationships are generated for dose (X-axis) vs. % Max (Y-axis) for active compounds using a non-linear regression computer program (PS-NONLIN), and $IC_{50}$ values with corresponding 95% confidence intervals are estimated from 50% of maximal attachment.

Reference Compounds

Various Arginine-Glycine-Aspartic Acid (RGD)-containing peptides, and monoclonal antibodies were assessed for the ability to inhibit osteopontin-$\alpha_v\beta_3$ attachment and the corresponding $IC_{50}$ values with 95% confidence intervals were generated in the SK-MEL-24 human malignant melanoma cell line; peptide structures are given by the standard single letter designation for amino acids:

| SEQ ID NO. | PEPTIDE | IC50 | 95% confidence interval |
|---|---|---|---|
| 7 | GPenGRGDSPCA | 0.58 mM | 0.51 to 0.67 |
| 8 | n-Me-GRGDSP | 4.0 mM | 3.4 to 4.7 |
| 1 | GRGDSP | 4.1 mM | 3.4 to 4.9 |
| 2 | GRGDTP | 5.2 mM | 3.4 to 4.9 |

| Antibody | Dilution | % Max Attachment (mean ± SD) |
|---|---|---|
| $a_vb_5$ (P1F6) | 1:1000 | 111 ± 3.3 |
|  | 1:100 | 112 ± 2.6 |
|  | 1:10 | 111 ± 3.3 |
| $a_vb_3$ (LM609) | 1:1000 | 0 |
|  | 1:100 | 5.1 ± 1.7 |

LITERATURE REFERENCES

Ruoslahti, R. Fibronectin and its receptors. Ann. Rev. Biochem. 57:375–413, 1988.

Hynes, R. O. Integrins: Versatility, modulation, and signaling in cell adhesion. Cell. 69: 11–25, 1992.

Osteoclast Pitting Assay

The assay is conduct ed as described in Murrills and Dempster (1990) Bone 11:333–344. Briefly, 4×4×0.2 mm slices of devitalized bovine cortical bone are numbered, placed in the wells of 96-well culture plates and wetted with 100 ul of Medium 199 containing Hanks salts, 10 mM HEPES, pH 7.0 (Medium 199/Hanks). Bone cell suspensions containing osteoclasts are prepared by mincing the long bones of neonatal rats (Sprague-Dawley, 4–6 days old) in Medium 199/Hanks. 100 uL of the suspension are then plated onto each slice and incubated 30 minutes to allow osteoclasts to adhere. The slices are rinsed to remove non-adherent cells and incubated 24 h in Medium 199 containing Earle's salts, 10 mM HEPES and 0.7 g/L $NaHCO_3$, which equilibrates at pH 6.9 in a 5% $CO_2$ atmosphere. At this pH the adherent osteoclasts excavate an adequate number of resorption pits for assay purposes. Slices are fixed in 2.5% glutaraldehyde and osteoclasts counted following tartrate-resistant acid phosphatase staining. In experiments in which osteoclast numbers are significantly reduced in a particular treatment, a check is made for non-specific cytotoxicity by counting the number of contaminant fibroblast-like cells following toluidine staining. All cells are stripped from the slice by sonication on 0.25M $NH_4OH$ and the resorption pits formed by the osteoclasts during the experiment stained with toluidine blue. Resorption pits are quantified by manually counting.

Statistics

The experiments are conducted according to a block design with osteoclasts from each animal exposed to each treatment. Three replicate slices are used per treatment per animal, such that a total of 96 slices are examined for an experiment involving four animals and eight treatments (including control). Several parameters are recorded on a "per slice" basis: number of pits, number of osteoclasts, number of pits per osteoclast, number of fibroblast-like bone cells. SAS or JMP statistical software are used for statistical analysis. If analysis of variance reveals significant effects in the experiment, those treatments differing significantly from control are identified using Dunnett's test. $IC_{50}$s are calculated for active compounds using dose-response curves.

Reference Compound: Rat Calcitonin

Clinical Relavence

Osteoclasts are responsible for the bone loss that occurs in the onset of osteoporosis and anti-resorptive drugs directed against the osteoclast are a requirement for patients losing bone. Calcitonin and bisphosphonates, both used as anti-resorptives in the clinic, show significant osteoclast inhibitory activity in this assay. Hence it is a reasonable assay in which to identify novel anti-resorptives.

Specific procedures are described in the following experimental examples. These examples are given to illustrate the invention and should not be construed as limiting the invention set forth in the appended claims.

EXAMPLE 1

Preparation of 3-(4,4-dimethyl-2,6dioxocylohex-1-ylideneethyl)amino-2-(Fluorenylmethyloxycarbonyl)amino-propionic Acid on Wang Resin (1)

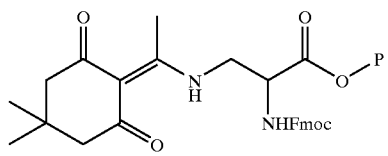
(1)

Wang resin (Wang, S. J. Am. Chem. Soc. 1973, 95, 1328–1333) (Advanced ChemTech 200–400 mesh, 1% crosslinked; loading: 1.2 mmol/g; 5 g, 4.6 mmol) was swollen in N,N-dimethylformamide (DMF) (20 mL). A solution of N-α-fmoc-N-β-1-(4,4-dimethyl-2,6-dioxocyclohex-1-ylidene)ethyl-L-diaminopropionic acid (Fmoc-Dpr(Dde)-OH) (Nova Biochem) (4.513 g; 9.2 mmol) in DMF (30 mL) was treated with N-hydroxybenzotriazole (HOBT) (1.242 g; 9.2 mmol), 2-(1H-benzotriazolc-1-yl)-1,1,3,3-tetramethyluronium hexafluorophosphate (HBTU) (3.487 g; 9.2 mmol) and N,N-diisopropylethylamine (DIEA) (3.2 mL; 18.4 mmol) and added to the resin. The mixture was shaken at room temperature for 8 h. The mixture was filtered and the resin was washed with DMF (3×40 mL), methanol (MeOH) (3×40 mL) and dichloromethane (DCM) (3×40 mL). The resin was dried in vacuo to give 7.462 g. Resin Loading: 1.01 mmol/g.

EXAMPLE 2

Preparation of 2-Amino-3-(4,4-dimethyl-2,6-dioxocylohex-1-ylideneethyl)amino-propionic Acid on Wang Resin (2)

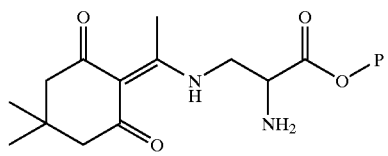
(2)

The resin prepared according to example 1 (7.085 g) in DMF was treated with 20% piperidine in DMF (40 mL) for 10 min and filtered. Another 40 mL portion of 20% piperidine in DMF was added to the resin and shaken at room temperature for 20 min. The resin was filtered and washed with DMF (3×40 mL), MeOH (3×40 mL) and DCM (3×40 mL). The resin was dried in vacuo.

EXAMPLE 3

Parallel Synthesis of 3-(4,4-dimethyl-2,6-dioxocylohex-1-ylideneethyl)amino-propionic acid 2-carbamates on Wang Resin (3)

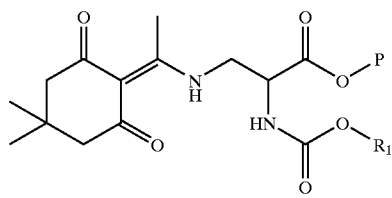
(3)

Fourteen compounds were synthesized in parallel using custom made manual synthesizer using fitted syringes as reaction vessels. The resin prepared according to the example 2 was placed in the reaction vessel (750 mg per vessel; 0.75 mmol). The resin in each vessel was swollen with dichloromethane. To each vessel was added diisopropylethylamine (969 mg; 1.3 mL; 7.5 mmol). Methyl chloroformate (283.5 mg; 3 mmol) was added to vessel 1; Ethyl chloroformate (325.6 mg; 3 mmol) was added to vessel 2; n-Propyl chloroformate (367.7 mg; 3 mmol) was added to vessel 3; i-Propyl chloroformate (367.7 mg; 3 mmol) was added to vessel 4; Allyl chloroformate (361.6 mg; 3 mmol) was added to vessel 5; 3-Butenyl chloroformate (403.7 mg; 3 mmol) was added to vessel 6; Propargyl chloroformate (355.6 mg; 3 mmol) was added to vessel 7; n-Hexyl chloroformate (493.9 mg; 3 mmol) was added to vessel 8; Octyl chloroformate (578.1 mg; 3 mmol) was added to vessel 9; Neopentyl chloroformate (451.8 mg; 3 mmol) was added to vessel 10; 2,2,2-Trichloroethyl chloroformate (635.6 mg; 3 mmol) was added to vessel 11; n-Butyl chloroformate (409.7 mg; 3 mmol) was added to vessel 12; i-Butyl chloroformate (409.7 mg; 3 mmol) was added to vessel 13; Benzyl chloroformate (511.8 mg; 3 mmol) was added to vessel 14. The reaction vessels were shaken at room temperature using orbital shaker (Thermolyne RotoMix Type 50800) for 18 h. The mixtures were filtered and the resin in each vessel was washed with dichloromethane (4×4 mL), methanol (4×mL) and dichloromethane (2×4 mL). The resins were dried under vacuum. A sample of resin from each vessel was removed and subjected to Kaiser Ninhydrin test. If the test showed the presence of free amine (resin turned blue) the coupling described above was repeated.

A sample of the resin was removed from reaction vessel 10 and subjected to cleavage with dichloromethane (0.5 mL) and trifluroacetic acid (0.5 mL) for 30 min at room temperature. The reaction mixture was filtered and the resin was washed with dichloromethane. The filtrate was concentrated and dried in vacuo on a Savant Speed Vac Plus. The product was characterized by HPLC: 4.28 min (82% @ 220 nm); MS: 383 $(M+H)^+$.

EXAMPLE 4

Parallel Synthesis of 3-Aminopropionic acid 2-carbamates on Wang Resin (4)

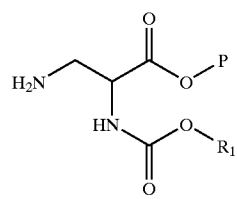
(4)

All the Fourteen reaction vessels containing 3-(4,4-dimethyl-2,6-dioxocylohex-1-ylideneethyl)amino-propionic acid 2-carbamates on Wang Resin (3) prepared according to the example 3 were shaken: with a solution of 2% hydrazine in dimethylformamide (3mL) for 5 min. at room temperature. The reaction mixture was filtered and an additional 3 mL of a solution of 2% hydrazine in dimethylformamide was added and the reaction vessels were shaken at room temperature for 5 min. The mixtures were filtered and the resin in each vessel was washed with dimethylformamide (4×4 mL), methanol (4×mL) and dichloromethane (4×4 mL). The resins were dried under vacuum. A sample of resin from each vessel was removed and subjected to Kaiser Ninhydrin test for the presence of free amine (resin turns blue).

A sample of the resin was removed from reaction vessel 10 and subjected to cleavage with dichloromethane (0.5 mL) and trifluroacetic acid (0.5 mL) for 30 min at room temperature. The reaction mixture was filtered and the resin was washed with dichloromethane. The filtrate was concentrated and dried in vacuo on a Savant Speed Vac Plus. The product was characterized by HPLC: 4.686 min (78% @ 220 nm); MS: 219 (M+H)$^+$.

EXAMPLE 5

Preparation of 4-[(2-fluorenylmethyloxycarbonyl-amino)ethoxy]-2-hydroxybenzoic acid (15)

The compound was prepared as shown in Scheme II.

The detailed synthetic procedures is described in the following Steps 1–3.

STEP 1

Methyl 4-[2-N-(t-butoxycarbonyl)ethoxy]-2-hydroxy benzoate (13)

Methyl 2,4-dihydroxy benzoate (14.5 g, Aldrich), 2-(N-t-butoxycarbonyl)ethanol (13.9 g, Aldrich) and triphenyl phosphine (22.6 g, Aldrich) were combined in 350 mL of THF and cooled in ice under $N_2$ atmosphere. Diethyl diazodicarboxylate (DEAD) (15 g, Aldrich) was added, the ice bath removed and the reaction mixture allowed to stir at ambient temperature for 15 h. The solvent was removed on a rotary evaporator and the residue chromatographed on silica gel (300 g, Merck silica 60), elution with $CH_2Cl_2$ to give 18 g of methyl 4-[2-N-(t-butoxycarbonyl)ethoxy]-2-hydroxy benzoate, as a viscous oil. NMR (300 MHz, $CDCl_3$) d 11.0 (s, 1 H), 9.5 (d, J=8 Hz, 1H), 6.4 (m, 2H), 5.0 (broad, 1H), 4.0 (t, J=5 Hz, 2H), 3.91 (s, 3H), 3.54 (m, 2H), 1.45 (s, 9H), MS (+ESI) m/z 334 (M+Na)$^+$.

STEP 2

4-(2-Aminoethoxy)-2-hydroxybenzoic acid, hydrochloride (14)

Ester (13) (7.2 g) from Step 1 was treated with 5eq. KOH (dissolved in minimum amount of water and equal volume of 1,4-dioxane) at room temperature until TLC indicated complete absence of starting material (3–12 h). The reaction mixture was acidified (pH=6) with the addition of 1N HCl solution and extracted with ethyl acetate. The extract was washed with saturated aqueous brine solution, dried over $MgSO_4$, filtered and concentrated on the rotary evaporator. The crude product (5.34 g) was recrystallized from ether, then dissolved in 1,4-dioxane and treated with an excess of anhydrous HCl (4M in dioxane, Aldrich). The mixture was allowed to stand at ambient temperature for 24 h. Volatile materials were removed in vacuo on the rotary evaporator to give as a hydroscopic off-white solid. NMR (400 MHz, Scheme II

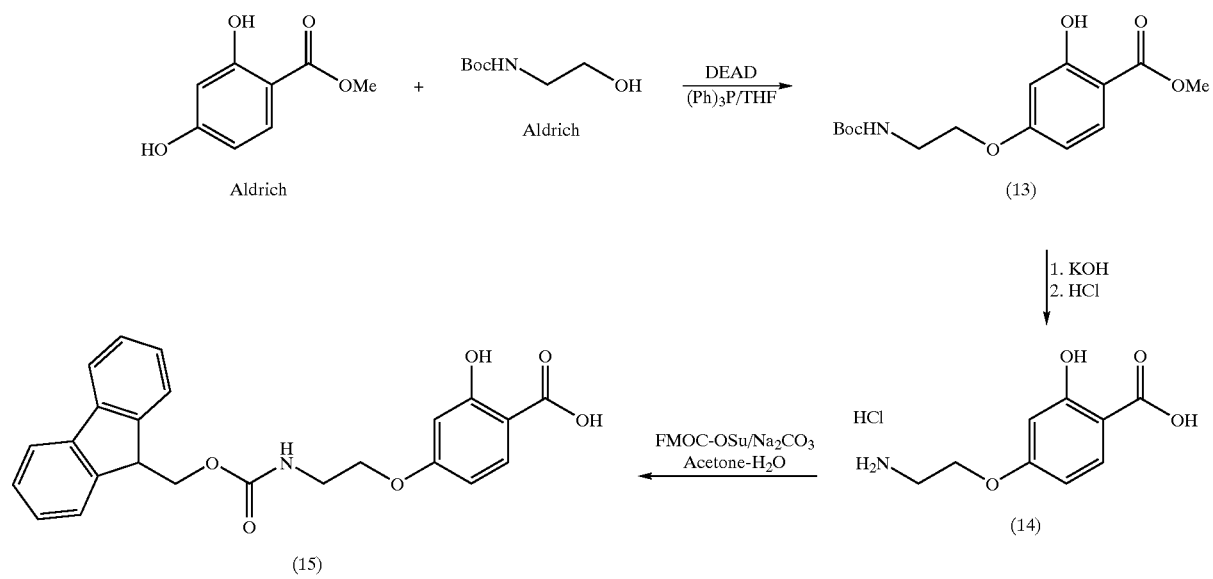

DMSO-d6) d 13.6 (broad, 1H), 11.6 (broad, 1H), 8.3 (broad, 3H), 7.7 (d, J=9 Hz, 2H), 6.53 (m, 2H), 4.23 (t, J=5 Hz, 2H), 3.2 (s, broad, 2H).

STEP 3

4-[(2-fluorenylmethyloxycarbonylamino)ethoxy]-2-hydroxybenzoic acid (15)

The Amino acid (14) (1.864 g; 8 mmol) from Step 2 was dissolved in 1:1 acetone—water (50 mL) containing Sodium Carbonate (1.696 g; 16 mmol). To the solution was added Fmoc-Osu (2.696 g; 8 mmol) in acetone (25 mL) dropwise at room temperature. The solution was stirred at room temperature for 18 h. The reaction mixture was concentrated and the residue was dissolved in water and extracted with ether (2×50 mL). The aqueous layer was cooled in an ice bath and acidified with 6N HCl to pH 3. The solid obtained was filtered and washed with water and dried under vacuo (3.22 g). NMR (300 MHz, DMSO-d6) δ7.9 (d, 2H), 7.65–7.75 (m, 2H), 7.55 (t, 2H), 7.4 (t, 2H), 7.3 (t, 2H), 6.5 (m, 2H), 4.35 (d, 2H), 4.25 (t, 1H), 4.05 (t, 2H), 3.4 (t, 2H).

EXAMPLE 6

Parallel Synthesis of 3-[4-(2-fluorenylmethyloxycarbonylaminoethoxy-2-Hydroxy)-benzoylamino]-propionic acid 2-carbamates on Wang Resin (6)

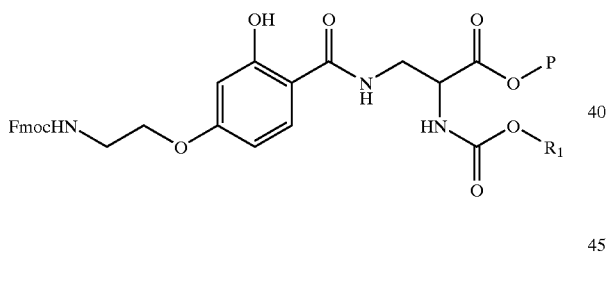

(6)

All the Fourteen reaction vessels containing 3-aminopropionic acid 2-carbamates on Wang Resin (4) prepared according to the example 4 were washed with DMF to swell the resin. A solution of 4-[(2-fluorenylmethyloxycarbonyl-amino)ethoxy]-2-hydroxybenzoic acid (15) (628.5 mg; 1.5 mmole) prepared as shown in Scheme II, example 5 in DMF was mixed with diisopropylcarbodiimide (189 mg; 1.5 mmole), hydroxybenzotriazole (202.5 mg; 1.5 mmole) and dimethylaminopyridine (18.33 mg; 0.15 mmole) and the mixture was added each reaction vessel. The reaction vessels were shaken at room temperature for 16 h. The mixtures were filtered and the resin in each vessel was washed with dimethylformamide (4×4 mL), methanol (4×mL) and dichloromethane (4×4 mL). The resins were dried under vacuum. A sample of resin from each vessel was removed and subjected to Kaiser Ninhydrin test. If the test showed the presence of free amine (resin turned blue) the coupling described above was repeated.

EXAMPLE 7

Parallel Synthesis of 3-[4-(2-aminoethoxy)-2-hydroxy-benzoylamino]-propionic acid 2-carbamates on Wang Resin (7)

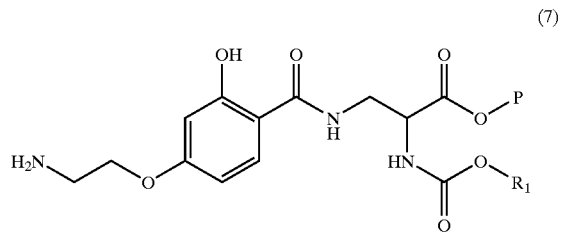

(7)

All the Fourteen reaction vessels containing 3-[2-Hydroxy-4-(2-aminoethoxy)benzoylamino]-propionic acid 2-carbamates on Wang Resin (6) prepared according to the example 6 were shaken with a solution of 20% piperidine in DMF (5 mL) for 10 min and filtered. Another 5 mL portion of 20% piperidine in, DMF was added and shaken at room temperature for 20 min. The resin in each vessel was filtered and washed with DMF (3×40 mL), MeOH (3×40 mL) and DCM (3×40 mL). The resins were dried under vacuum.

A sample of the resin was removed from reaction vessel 10 and subjected to cleavage with dichloromethane (0.5 mL) and trifluroacetic acid (0.5 mL) for 30 min at room temperature. The reaction mixture was filtered and the resin was washed with dichloromethane. The filtrate was concentrated and dried in vacuo on a Savant Speed Vac Plus. The product was characterized by HPLC: 3.35 min (70% @ 220 nm); MS: 398 (M+H)$^+$.

EXAMPLE 8

Parallel Synthesis of 3-[4-(2-guanidinoethoxy)-2-hydroxy-benzoylamino]-propionic acid 2-carbamates

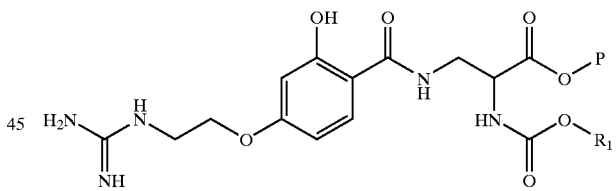

A sample 100 mg of resin (1.1 mmole) from each of the reaction vessels in Example 7 was transferred to 14 new reaction vessels and the resin was swollen in DMF. To each vessel was added a solution of 1,3-bis(tert-butoxycarbonyl)-2-methyl-2-thiopseudourea (145 mg; (0.5 mmole) in DMF (1.5 mL) followed by diisopropylamine (0.15 mL; 1 mmole). The reaction vessels were shaken at room temperature for 18 h. The mixtures were filtered and the resin in each vessel was washed with dimethylformamide (4×4 mL), methanol (4×mL) and dichloromethane (4×4 mL). The resins were dried under vacuum. A sample of resin from each vessel was removed and subjected to Kaiser Ninhydrin test. If the test showed the presence of free amine (resin turned blue) the coupling described above was repeated.

The product was cleaved from the resin by treatment with dichloromethane (0.5 mL) and trifluroacetic acid (0.5 mL) for 30 min at room temperature. The reaction mixture was filtered and the resin was washed with dichloromethane. The filtrate was concentrated and dried in vacuo on a Savant Speed Vac Plus. This crude material was purified via preparative HPLC. The LC and MS data for all the compounds isolated (A4–N4) are shown in the Table 2. Representative compounds were characterized by 1 H NMR.

2(S)-(2,2-Dimethyl-propoxycarbonylamino)-3-[4-(2-guanidino-ethoxy)-2-hydroxy-benzoylamino]-propionic acid (J4): NMR (300 MHz, MeOH-d4) δ7.7 (d, J=7 Hz, 1H), 6.5 (m, 2H), 4.5 (q, 1H), 4.2 (m, 2H), 3.85 (m, 1H), 3.8 (m, 2H), 3.75 (m, 1H), 3.7 (m, 2H), 0.9 (s, 9H).

HR-MS FAB m/z for $C_{19}H_{29}N_5O_7$ calcd. 440.2145 ($M^+$+1), obsd. 440.2154.

2(S)-Benzyloxycarbonylamino-3-[4-(2-guanidino-ethoxy)-2-hydroxy-benzoylamino]-propionic acid (N4): NMR (300 MHz, DMSO-d6) δ12.8 (s, 1H), 8.8 (t, J=8 Hz, 1H), 7.8 (d, J=9 Hz, 1H), 7.7 (m, 1H), 7.3 (m, 5H), 7.25 (m, 1H), 6.5 (m, 2H), 5.1 (s, 2H), 4.25 (q, 1H), 4.1 (t, 2H), 3.8 (m, 3H), 3.7 (m, 1H), 3.5 (m, 2H).

EXAMPLE 9

Parallel Synthesis of 3-{4-[2-(4,5-dihydroimidazole-2-ylamino)-ethoxy]-2-hydroxy-benzoylamino}-propionic acid 2-carbamates

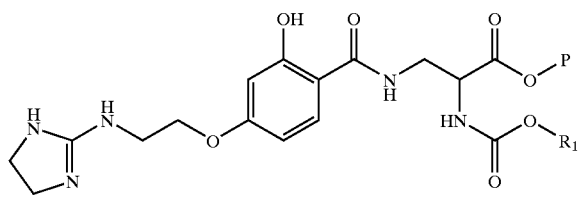

A sample 100 mg of resin (0.1 mmole) from each of the reaction vessels in Example 7 was transferred to 14 new reaction vessels and the resin was swollen in DMF. To each vessel was added a solution of 2-(3,5-dimethylpyrazolyl)-4,5-dihydroimidazole hydrobromide (123 mg; 0.5 mmole) in DMF (1.5 mL) followed by diisopropylamine (0.15 mL; 1 mmole). The reaction vessels were shaken at 60° C. for 18 h. The mixtures were filtered and the resin in each vessel was washed with dimethylformamide (4×4 mL), methanol (4×mL) and dichloromethane (4×4 mL). The resins were dried under vacuum. A sample of resin from each vessel was removed and subjected to Kaiser Ninhydrin test. If the test showed the presence of free amine (resin turned blue) the coupling described above was repeated.

The product was cleaved from the resin by treatment with dichloromethane (0.5 mL) and trifluroacetic acid (0.5 mL) for 30 min at room temperature. The reaction mixture was filtered and the resin was washed with dichloromethane. The filtrate was concentrated and dried in vacuo on a Savant Speed Vac Plus. This crude material was purified via preparative HPLC. The LC and MS data for all the compounds isolated (A5–N5) are shown in the Table 2. Representative compounds were characterized by 1H NMR.

3-{4-[2-(4,5-dihydroimidazole-2-ylamino)-ethoxy]-2-hydroxy-benzoylamino}-2-(2,2-dimethyl-propoxycarbonylamino)-propionic acid (J5): NMR (300 MHz, MeOH-d4) δ7.7 (d, J=7 Hz, 1H), 6.5 (m, 2H), 4.5 (q, 1H), 4.2 (t, 2H), 3.85 (m, 1H), 3.75–3.8 (m, 7H), 3.5 (t, 2H), 0.9 (s, 9H).

HR-MS FAB m/z for $C_{21}H_{31}N_5O_7$ calcd. 466.2302 ($M^+$+1), obsd. 466.2289.

EXAMPLE 10

Parallel Synthesis of 3-{2-hydroxy-4-[2-(4,5,6,7-tetrahydro-3H-azepin-2-ylamino)-ethoxy]-benzoylamino}-propionic acid 2-carbamates

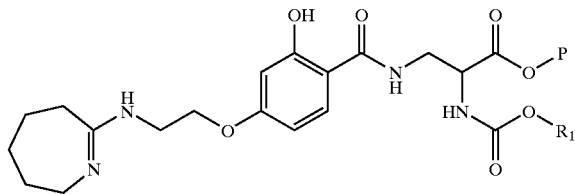

A sample 100 mg of resin (0.1 mmole) from each of the reaction vessels in Example 7 was transferred to 14 new reaction vessels and the resin was swollen in dioxane. To each vessel was added a solution of 1-aza-2-methoxy-1-cycloheptene (127 mg; 1 mmole) in dioxane (1.5 mL). The reaction vessels were shaken at room temperature for 18 h. The mixtures were filtered and the resin in each vessel was washed with dioxane (4×4 mL), methanol (4×mL) and dichloromethane (4×4 mL). The resins were dried under vacuum. A sample of resin from each vessel was removed and subjected to Kaiser Ninhydrin test. If the test showed the presence of free amine (resin turned blue) the coupling described above was repeated.

The product was cleaved from the resin by treatment with dichloromethane (0.5 mL) and trifluroacetic acid (0.5 mL) for 30 min at room temperature. The reaction mixture was filtered and the resin was washed with dichloromethane. The filtrate was concentrated and dried in vacuo on a Savant Speed Vac Plus. This crude material was purified via preparative HPLC. The LC and MS data for all the compounds isolated (A6–N6) are shown in the Table 2. Representative compounds were characterized by 1H NMR.

2-(2,2-Dimethyl-propoxycarbonylamino)-3-{2-hydroxy-4-[2-(4,5,6,7-tetrahydro-3H-azepin-2-ylamino)-ethoxy]-benzoylamino}-propionic acid (N6): NMR (300 MHz, DMSO-d6) δ12.8 (s, 1H), 9.55 (t, 1H), 9.25 (t, 1H), 8.8 (t, 1H), 7.8 (d, J=9 Hz, 1H), 7.7 (d, J=8 Hz, 1H), 7.3 (m, 5H), 6.5 (m, 2H), 5.0 (s, 2H), 4.3 (q, 1H), 4.2 (t, 2H), 3.8 (m, 3H), 3.6 (m, 1H), 3.5 (m, 2H), 2.7 (m, 2H), 1.7 (m, 2H), 1.6 (m, 4H),

EXAMPLE 11

Parallel Synthesis of 3-{4-[2-(3-benzylureido)-ethoxy]-2-hydroxy-benzoylamino}-propionic acid 2-carbamates

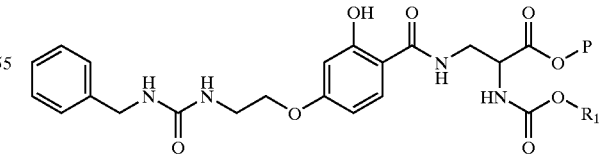

A sample 100 mg of resin (0.1 mmole) from each of the reaction vessels in Example 7 was transferred to 14 new reaction vessels and the resin was swollen in 1:1 Tetrahydrofuran and dichloromethane. To each vessel was added a solution of 4-nitrophenylchloroformate (50 mg; 0.25 mmole) in 1:1 THF: DCM (1.5 mL) followed by diisopropylamine (0.075 mL; 0.5 mmole). The reaction vessels were shaken at room temperature for 30 min. The mixtures were filtered and the resin in each vessel was washed with THF (4×4 mL) and dichloromethane (4×4 mL) and dried. The resin in each vessel was suspended in DMF (1.5 mL) and benzyl amine (54 mg; 0.5 mmole) was added followed by triethylamine (101 mg; 1 mmole). The mixtures were filtered and the resin in each vessel was washed with dimethylformamide (4×4 mL), methanol (4×mL) and dichloromethane (4×4 mL). The resins were dried under vacuum.

The product was cleaved from the resin by treatment with dichloromethane (0.5 mL) and trifluroacetic acid (0.5 mL) for 30 min at room temperature. The reaction mixture was filtered and the resin was washed with dichloromethane. The filtrate was concentrated and dried in vacuo on a Savant Speed Vac Plus. This crude material was purified via preparative HPLC. The LC and MS data for all the compounds isolated (A1–N1) are shown in the Table 2. Representative compounds were characterized by 1H NMR.

3-{4-[2-(3-benzylureido)-ethoxy]-2-hydroxy-benzoylamino}-2-(2,2-dimethyl-propoxycarbonylamino)-propionic acid (J1): NMR (300 MHz, MeOH-d4) δ7.65 (d, J=7 Hz, 1H), 7.25 (m, 5H), 6.5 (m, 2H), 4.4 (q, 1H), 4.3 (s, 2H), 4.15 (t, 2H), 3.85 (m, 1H), 3.75 (m, 3H), 3.5 (t, 2H), 0.9 (s, 9H).

HR-MS FAB m/z for $C_{26}H_{34}N_4O_8$ calcd. 531.2455 ($M^+$+1), obsd. 531.2459.

EXAMPLE 12

Parallel Synthesis of 3-{2-hydroxy-4-[2-(3-pyridin-3-ylmethyl-ureido)-ethoxy]-benzoylamino}-propionic acid 2-carbamates

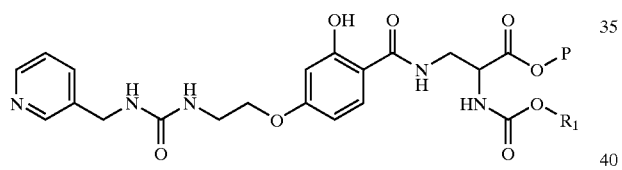

Compounds A3–N3 were prepared by following the procedure detailed in example 12, by employing 3-pyridylmethylamine in the place of benzyl amine. The LC and MS data for all the compounds isolated (A3–N3) are shown in the Table 2.

EXAMPLE 13

Parallel Synthesis of 3-{2-hydroxy-4-[2-(3-pyridin-4-ylmethyl-ureido)-ethoxy]-benzoylamino}-propionic acid 2-carbamates

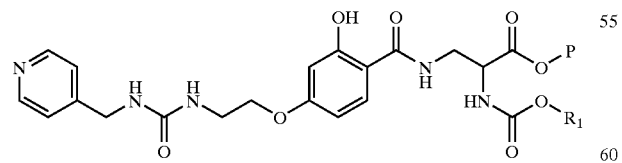

Compounds A2–N2 were prepared by following the procedure detailed in example 12, by employing 4-pyridylmethylamine in the place of benzyl amine. The LC and MS data for all the compounds isolated (A2–N2) are shown in the Table 2.

EXAMPLE 14

Preparation of 4-[(2-fluorenylmethyloxycarbonylamino)ethoxy]-2-hydroxybenzoic acid (4)

The compound was prepared as shown in Scheme III.

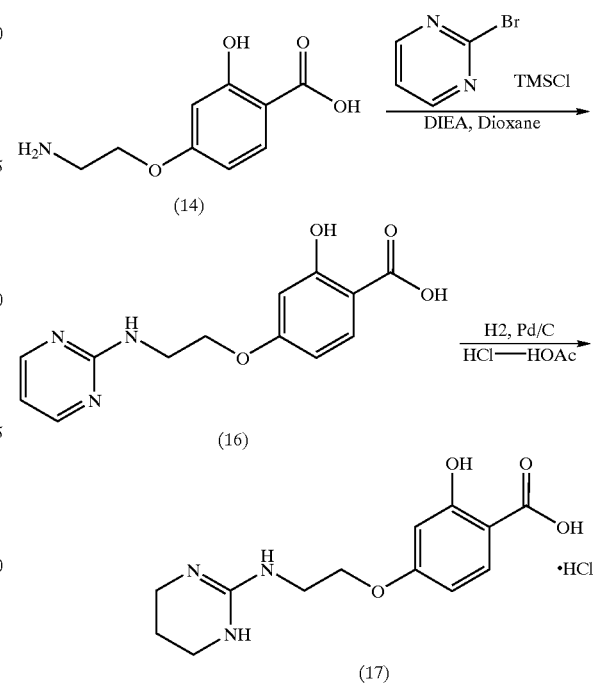

The detailed synthetic procedures is described in the following 2 steps.

STEP 1

2-Hydroxy-4-[2-(pyrimidine-2ylamino)ethoxy] benzoic acid (16)

A mixture of compound (14) (20 g), dissopropylethylamine (74 mL), trimethylsilylchloride (21.6 mL) and 2-bromopyrimidine (Lancaster, 13.5 g) were combined in 350 mL 1,4-dioxane at room temperature, then brought to reflux under $N_2$ atmosphere. After 2 days, an additional 12 mL silylchloride was added, and the mixture continued at reflux for an additional 2 days (until TLC showed no starting material remained). The reaction mixture was cooled to ambient temperature, concentrated to dryness in vacuo on a rotary evaporator and the residue suspended in water. The heterogeneous mixture was refluxed briefly, allowed to cool to room temperature, the product collected on a vacuum filter and air dried to give 15.3 g of (16), as a tan powder. NMR (400 MHz, DMSO-$d_6$) d 12 (very broad, 2H) 8.3 (d, J=5 Hz, 2H) 7.7 (d, J=9 Hz, 1H), 7.28 (t, J=6 Hz, 1H), 6.57 (t, J=5 Hz, 1H), 6.49 (m, 2H), 4.13 (t, J=6 Hz, 2H), 3.62 (q, 2H); MS (+ESI) m/z 276 (M+H)$^+$; IR (KBr) n (cm$^{-1}$) 3275, 3000, 1660, 1625.

STEP 2

2-Hydroxy-4-[2-(3,4,5,6-tetrahydropyrimidin-zylamino)ethoxy]-benzoic acid (17)

Compound (16) (2 g) was combined with 10% Pd/C (0.5 g), acetic acid (100 mL) and concentrated hydrochloric acid (0.7 mL). The mixture was stirred at room temperature under an atmosphere of $H_2$ (balloon) for 2 days. Celite was added and the mixture stirred for 0.5 h, then filtered through a pad of celite with the aid of isopropanol. Volatile materials were removed on the rotary evaporator and the residue warmed with heptane (~0.5 h, 100° C.) followed by concentration in vacuo to give (17) as a tan foam. NMR (400 MHz, DMSO-$d_6$) δ12.9 (broad, 2H), 8.25 (s, broad, 2H), 7.85 (t, J=6 hz, 1H), 7.66 (d, J=9 Hz, 1H), 6.48–6.41 (m, 2H), 4.07 (t, J=5 Hz, 2H), 3.56–3.50 (m, 2H), 3.22 (m, 2H, overlapping with $H_2O$ peak), 1.79 (m, 2H); IR (KBr) n ($cm^{-1}$) 3450 (broad); MS (+ESI) m/z 280 $(M+H)^+$.

EXAMPLE 15

Parallel Synthesis of 3-{2-Hydroxy-4-[2-(1,4,5,6-tetrahydropyrimidin-2-ylamino)-ethoxy]-benzoylamino}-propionic acid 2-carbamates

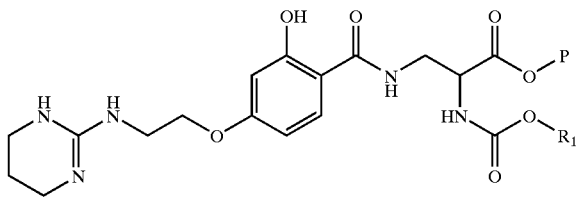

A 100 mg sample of all fourteen 3-aminopropionicacid 2-carbamates (4) on Wang resin synthesized as detailed in example 4 were individually washed with DMF to swell the resin. A solution of 2-hydroxy-4-[2-(3,4,5,6-tetrahydropyrimidin-2-ylamino)ethoxy]-benzoic acid (17) (70 mg; 0.25 mmole) prepared as shown in Scheme III, example 14 in DMF was mixed with diisopropylcarbodiimide (32 mg; 0.25 mmole), hydroxybenzotriazole (38 mg; 0.25 mmole) and dimethylaminopyridine (3 mg; 0.025 mmole) and the mixture was added each reaction vessel. The reaction vessels were shaken at room temperature for 16 h. The mixtures were filtered and the resin in each vessel was washed with dimethylformamide (4×4 mL), methanol (4×mL) and dichloromethane (4×4 mL). The resins were dried under vacuum. A sample of resin from each vessel was removed and subjected to Kaiser Ninhydrin test. If the test showed the presence of free amine (resin turned blue) the coupling described above was repeated.

The product was cleaved from the resin by treatment with dichloromethane (0.5 mL) and trifluroacetic acid (0.5 mL) for 30 min at room temperature. The reaction mixture was filtered and the resin was washed with dichloromethane. The filtrate was concentrated and dried in vacuo on a Savant Speed Vac Plus. This crude material was purified via preparative HPLC. The LC and MS data for all the compounds isolated (A7–N7) are shown in the Table 2. Representative compounds were characterized by 1H NMR.

2-(2,2-Dimethyl-propoxycarbonylamino)-3-{2-hydroxy-4-[2-(1,4,5,6-tetrahydropyrimidin-2-ylamino)-ethoxy]-benzoylamino}-propionic acid (J7): NMR (400 MHz, MeOH-d4) δ7.7 (d, J=7 Hz, 1H), 6.5 (m, 2H), 4.45 (q, 1H), 4.1 (t, 2H), 3.8–3.65 (m, 4H), 3.55 (t, 2H), 3.35 (t, 4H), 2.0 (m, 2H), 0.9 (s, 9H).

HR-MS FAB m/z for $C_{22}H_{33}N_5O_7$ calcd. 480.2458 ($M^+$+1), obsd. 480.2431.

TABLE 1

Parallel synthesis of various N-substituted Carbamates (I)

| R1 | Example 11 | Examle 13 | Ex. 12 | Ex. 8 | Ex. 9 | Ex. 10 | Ex. 15 |
|---|---|---|---|---|---|---|---|
| H₃C— | A1 | A2 | A3 | A4 | A5 | A6 | A7 |
| H₃C—\— | B1 | B2 | B3 | B4 | B5 | B6 | B7 |
| H₃C—\—\— | C1 | C2 | C3 | C4 | C5 | C6 | C7 |
| isobutyl | D1 | D2 | D3 | D4 | D5 | D6 | D7 |
| allyl | E1 | E2 | E3 | E4 | E5 | E6 | E7 |
| butenyl | F1 | F2 | F3 | F4 | F5 | F6 | F7 |
| pentynyl | G1 | G2 | G3 | G4 | G5 | G6 | G7 |
| heptyl | H1 | H2 | H3 | H4 | H5 | H6 | H7 |

TABLE 1-continued

Parallel synthesis of various N-substituted Carbamates (I)

| R1 | Example 11 | Examle 13 | Ex. 12 | Ex. 8 | Ex. 9 | Ex. 10 | Ex. 15 |
|---|---|---|---|---|---|---|---|
| H₃C-(CH₂)₇- | I1 | I2 | I3 | I4 | I5 | I6 | I7 |
| neopentyl | J1 | J2 | J3 | J4 | J5 | J6 | J7 |
| CCl₃-C(CH₃)- | K1 | K2 | K3 | K4 | K5 | K6 | K7 |
| H₃C-(CH₂)₃- | L1 | L2 | L3 | L4 | L5 | L6 | L7 |
| isopentyl | M1 | M2 | M3 | M4 | M5 | M6 | M7 |
| benzyl | N1 | N2 | N3 | N4 | N5 | N6 | N7 |

TABLE 2

LC[1] & MS Data for the Carbamates from parallel synthesis

| | | | | | | |
|---|---|---|---|---|---|---|
| A1 (475 M + H) | A2 (476 M + H) | A3 (476 M + H) | A4 (384 M + H) | A5 (410 M + H) | A6 (437 M + H) | A7 (424 M + H) |
| 3.84 min @ 254 | 2.84 min @ 254 | 2.84 min @ 254 | 2.75 min @ 254 | 2.82 min @ 254 | 3.08 min @ 254 | 2.92 min @ 254 |
| B1 (489 M + H) | B2 (490 M + H) | B3 (490 M + H) | B4 (397 M + H) | B5 (424 M + H) | B6 (451 M + H) | B7 (438 M + H) |
| 4.00 min @ 254 | 3.01 min @ 254 | 2.99 min @ 254 | 2.93 min @ 254 | 2.99 min @ 254 | 3.25 min @ 254 | 3.09 min @ 254 |
| C1 (503 M + H) | C2 (504 M + H) | C3 (504 M + H) | C4 (412 M + H) | C5 (438 M + H) | C6 (465 M + H) | C7 (452 M + H) |
| 4.21 min @ 254 | 3.20 min @ 254 | 3.19 min @ 254 | 3.15 min @ 254 | 3.21 min @ 254 | 3.46 min @ 254 | 3.30 min @ 254 |
| D1 (503 M + H) | D2 (504 M + H) | D3 (504 M + H) | D4 (412 M + H) | D5 (438 M + H) | D6 (465 M + H) | D7 (452 M + H) |
| 4.19 min @ 254 | 3.17 min @ 254 | 3.17 min @ 254 | 3.11 min @ 254 | 3.17 min @ 254 | 3.38 min @ 254 | 3.28 min @ 254 |
| E1 (501 M + H) | E2 (502 M + H) | E3 (502 M + H) | E4 (410 M + H) | E5 (436 M + H) | E6 (463 M + H) | E7 (450 M + H) |
| 4.14 min @ 254 | 3.12 min @ 254 | 3.12 min @ 254 | 3.05 min @ 254 | 3.13 min @ 254 | 3.37 min @ 254 | 3.21 min @ 254 |
| F1 (515 M + H) | F2 (516 M + H) | F3 (516 M + H) | F4 (424 M + H) | F5 (450 M + H) | F6 (477 M + H) | F7 (463 M + H) |
| 4.31 min @ 254 | 3.28 min @ 254 | 3.29 min @ 254 | 3.25 min @ 254 | 3.31 min @ 254 | 3.55 min @ 254 | 3.46 min @ 254 |
| G1 (499 M + H) | G2 (500 M + H) | G3 (500 M + H) | G4 (408 M + H) | G5 (434 M + H) | G6 (461 M + H) | G7 (448 M + H) |
| 4.06 min @ 254 | 3.01 min @ 254 | 3.02 min @ 254 | 2.95 min @ 254 | 3.01 min @ 254 | 3.27 min @ 254 | 3.18 min @ 254 |
| H1 (545 M + H) | H2 (546 M + H) | H3 (546 M + H) | H4 (454 M + H) | H5 (480 M + H) | H6 (507 M + H) | H7 (494 M + H) |
| 4.90 min @ 254 | 3.90 min @ 254 | 3.90 min @ 254 | 3.91 min @ 254 | 3.97 min @ 254 | 3.19 min @ 254 | 4.12 min @ 254 |
| I1 (573 M + H) | I2 (502 M + H) | I3 (574 M + H) | I4 Not Isolated | I5 (508 M + H) | I6 (535 M + H) | I7 (522 M + H) |
| 5.37 min @ 254 | 4.38 min @ 254 | 4.37 min @ 254 | | 4.49 min @ 254 | 4.67 min @ 254 | 4.62 min @ 254 |
| J1 (531 M + H) | J2 (532 M + H) | J3 (532 M + H) | J4 (440 M + H) | J5 (466 M + H) | J6 (493 M + H) | J7 (480 M + H) |
| 4.58 min @ 254 | 3.57 min @ 254 | 3.58 min @ 254 | 3.57 min @ 254 | 3.63 min @ 254 | 3.85 min @ 254 | 3.77 min @ 254 |
| K1 (593 M + H) | K2 (594 M + H) | K3 (594 M + H) | K4 (502 M + H) | K5 Not Isolated | K6 (553 M + H) | K7 (542 M + H) |
| 4.62 min @ 254 | 3.62 min @ 254 | 3.62 min @ 254 | 3.60 min @ 254 | | 3.89 min @ 254 | 3.81 min @ 254 |
| L1 (517 M + H) | L2 (518 M + H) | L3 (518 M + H) | L4 (426 M + H) | L5 (452 M + H) | L6 (479 M + H) | L7 (466 M + H) |
| 4.43 min @ 254 | 3.43 min @ 254 | 3.43 min @ 254 | 3.39 min @ 254 | 3.46 min @ 254 | 3.70 min @ 254 | 3.60 min @ 254 |
| M1 (517 M + H) | M2 (518 M + H) | M3 (518 M + H) | M4 Not Isolated | M5 (452 M + H) | M6 (479 M + H) | M7 (466 M + H) |
| 4.41 min @ 254 | 3.4 min @ 254 | 3.40 min @ 254 | | 3.44 min @ 254 | 3.67 min @ 254 | 3.58 min @ 254 |
| N1 (551 M + H) | N2 (552 M + H) | N3 (552 M + H) | N4 (460 M + H) | N5 (486 M + H) | N6 (513 M + H) | N7 (500 M + H) |
| 4.59 min @ 254 | 3.52 min @ 254 | 3.55 min @ 254 | 3.53 min @ 254 | 3.60 min @ 254 | 3.83 min @ 254 | 3.74 min @ 254 |

[1]LC Conditions: HP 1100, 23° C., 10 μL injected; Column: YMC-ODS-A 4.6X50 5 μ; Gradient A: 0.05% TFA/Water, B: 0.05% TFA/Acetonitrile; Time 0 & 1 min: 98% A & 2% B; 7 min: 10% A & 90% B; 8 min: 10% A & 90% B; 8.9 min: 98% A & 2% B; Post time 1 min; Flow rate 2.5 mL/min; Detection: 215 and 254 nm, DAD

EXAMPLE 16

Parallel Synthesis of 3-[4-(2-guanidinoethoxy)-2-hydroxy-benzoylamino]-propionic acid 2-ureas (I)

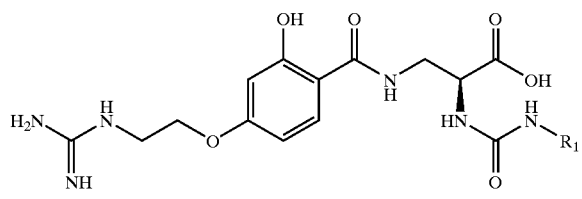

These compounds were prepared by following the procedures detailed in examples 1–8, but for example 3, wherein the chloroformates were replaced by isocyanates. The following Table shows the various isocyanates employed and the LC & MS data for the final products.

TABLE 3

| R1 | LC @ 254 nm | (M + H)+ |
|---|---|---|
| H₃C–(CH₂)₆– | 4.18 min | 481 |
| phenyl–CH₂– | 3.29 min | 445 |
| cyclohexyl–CH₂– | 3.32 min | 451 |
| phenyl–CH₂CH₂– | 3.20 min | 459 |
| 2-methylphenyl–CH₂– | 3.32 min | 459 |
| 4-methylphenyl–CH₂– | 3.50 min | 459 |
| 4-methoxyphenyl–CH₂– | 3.27 min | 475 |
| 2-methoxyphenyl–CH₂– | 3.36 min | 475 |

TABLE 3-continued

| R1 | LC @ 254 nm | (M + H)+ |
|---|---|---|
| 4-acetyl phenyl (H3C-C(O)-C6H4-) | 3.26 min | 487 |
| 2-chlorophenyl | 3.46 min | 481 |
| 2-bromophenyl | 3.48 min | 525 |
| 2-phenylphenyl | 3.81 min | 521 |
| 4-fluorophenyl | 3.39 min | 463 |
| 4-chlorophenyl | 3.68 min | 481 |
| 1-naphthyl | 3.57 min | 495 |
| phenethyl | 3.37 min | 473 |

TABLE 4

| R1 | LC @ 254 nm | (M + H)+ |
|---|---|---|
| n-pentyl | 3.20 min | 451 |
| n-heptyl | 3.69 min | 479 |
| n-nonyl | 4.24 min | 507 |
| allyl/butenyl | 2.84 min | 435 |
| cyclohexyl | 3.37 min | 477 |
| benzyl (PhCH2CH2-) | 3.26 min | 485 |
| 2-phenylcyclopropyl | 3.57 min | 511 |
| 2-methoxyphenyl | 3.42 min | 501 |
| 2-phenylphenyl | 3.89 min | 547 |
| phenethyl | 3.47 min | 499 |

EXAMPLE 17

Parallel Synthesis of 3-{4-[2-(4,5-dihydroimidazole-2-ylamino)-ethoxy]-2-hydroxy-benzoylamino}-propionic acid 2-ureas (I)

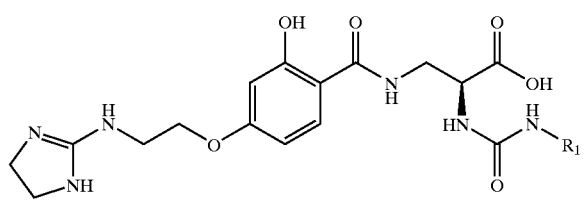

These compounds were prepared by following the procedures detailed in examples 1–7 and 9, but for example 3, wherein the chloroformates were replaced by isocyanates. The following Table 4 shows the various isocyanates employed and the LC & MS data for the final products.

EXAMPLE 18

Parallel Synthesis of 3-{2-hydroxy-4-[2-(1,4,5,6-tetrahydropyrimidin-2-ylamino)-ethoxy]benzoylamino}-propionic acid 2-ureas (I)

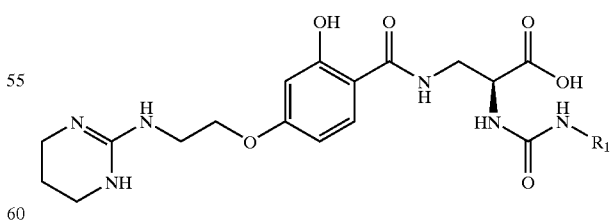

These compounds were prepared by following the procedures detailed in examples 1–4 and 15, but for example 3, wherein the chloroformates were replaced by isocyanates. The following Table 5 shows the various isocyanates employed and the LC & MS data for the final products.

TABLE 5

| R1 | LC @ 254 nm | (M + H)+ |
|---|---|---|
| H3C-CH2-CH2-CH2- | 3.30 min | 465 |
| H3C-(CH2)5- | 3.77 min | 493 |
| H3C-(CH2)7- | 4.31 min | 521 |
| CH2=CH-CH2-CH2- | 3.02 min | 449 |
| adamantyl-CH2- | 4.00 min | 543 |
| phenyl-CH2- | 3.42 min | 485 |
| cyclohexyl-CH2- | 3.45 min | 491 |
| (phenyl)CH2CH2- | 3.43 min | 499 |
| 4-methylphenyl-CH2- | 3.62 min | 499 |
| 2-methylphenyl-CH2- | 3.45 min | 499 |
| 2-methoxyphenyl-CH2- | 3.50 min | 515 |
| 2-methoxyphenyl-CH2- (isomer) | 3.39 min | 515 |
| 2-chlorophenyl-CH2- | 3.60 min | 521 |
| 2-bromophenyl-CH2- | 3.60 min | 565 |

TABLE 5-continued

| R1 | LC @ 254 nm | (M + H)+ |
|---|---|---|
| 2-phenylphenyl-CH2- | 3.95 min | 561 |
| 4-chlorophenyl-CH2- | 3.79 min | 521 |
| 1-naphthyl-CH2- | 3.67 min | 535 |
| phenyl-CH2-CH2-CH2- | 3.56 min | 513 |

EXAMPLE 19

Parallel Synthesis of 3-[4-(2-guanidinoethoxy)-2-hydroxy-benzoylamino]-propionic acid 2-amides (I)

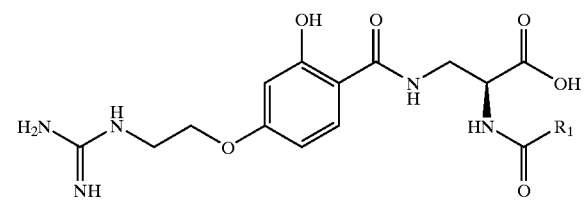

These compounds were prepared by following the procedures detailed in examples 1–8, but for example 3, wherein the following modified procedure was used.

Modified Procedure

The resin prepared according to the example 2 was placed in the reaction vessel (750 mg per vessel; 0.75 mmol). The resin in each vessel was swollen with DMF. A solution of appropriate carboxylic acid (1.5 mmole) in DMF was mixed with diisopropylcarbodiimide (189 mg; 1.5 mmole), hydroxybenzotriazole (202.5 mg; 1.5 mmole) and dimethylaminopyridine (18.33 mg; 0.15 mmole) and the mixture was added each reaction vessel. The reaction vessels were shaken at room temperature for 16 h. The mixtures were filtered and the resin in each vessel was washed with dimethylformamide (4×4 mL), methanol (4×mL) and dichloromethane (4×4 mL). The resins were dried under vacuum. A sample of resin from each vessel was removed and subjected to Kaiser Ninhydrin test. If the test showed the presence of free amine (resin turned blue) the coupling described above was repeated.

Table 6 shows the various carboxylic acids employed and the LC & MS data for the final products.

EXAMPLE 20

Parallel Synthesis of 3-{4-[2-(4,5-dihydroimidazole-2-ylamino)-ethoxy]-2-hydroxy-benzoylamino}-propionic acid 2-amides (I)

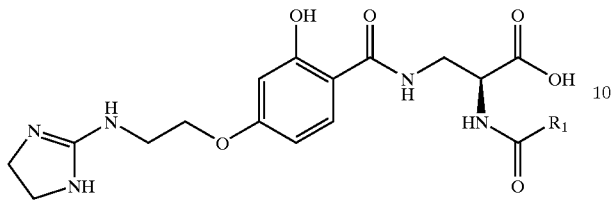

These compounds were prepared by following the procedures detailed in examples 1–7 and 9, but for example 3, wherein the above modified procedure was used. Table 6 shows the various carboxylic acids employed and the LC & MS data for the final products.

EXAMPLE 21

Parallel Synthesis of 3-{2-hydroxy-4-[2-(1,4,5,6-tetrahydropyrimidin-2-ylamino)-ethoxy] benzoylamino}-propionic acid 2-amides (I)

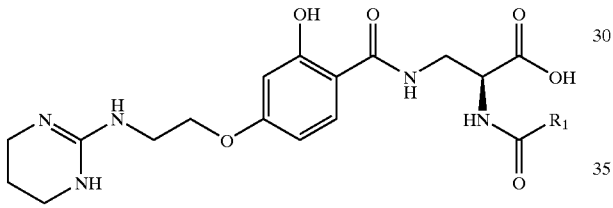

These compounds were prepared by following the procedures detailed in examples 1–4 and 15, but for example 3, wherein the above modified procedure was used. Table 6 shows the various carboxylic acids employed and the LC & MS data for the final products.

TABLE 6

LC & MS data for various N-substituted Amides

| | G | | |
|---|---|---|---|
| R1 | Guanidine LC & MS | Imidazole LC & MS | THP LC & MS |
| H₃C–⟨–⟩–CH₃ (isopropyl) | 2.88 min 396 (M + H) | 2.90 min 422 (M + H) | 3.03 min 436 (M + H) |
| H₃C–propyl | 2.88 min 396 (M + H) | 2.90 min 422 (M + H) | 3.03 min 436 (M + H) |
| H₃C–pentyl | 3.34 min 424 (M + H) | 3.34 min 450 (M + H) | 3.46 min 464 (M + H) |
| H₃C–butyl | 3.09 min 410 (M + H) | 3.10 min 436 (M + H) | 3.24 min 450 (M + H) |
| neopentyl (t-Bu-CH₂) | 3.24 min 424 (M + H) | 3.26 min 450 (M + H) | 3.37 min 464 (M + H) |
| tetramethylcyclopropyl | 3.70 min 450 (M + H) | 3.71 min 476 (M + H) | 3.79 min 490 (M + H) |
| adamantyl-ethyl | 3.85 min 502 (M + H) | 3.90 min 528 (M + H) | 3.98 min 542 (M + H) |
| butynyl | 2.84 min 406 (M + H) | 2.86 min 432 (M + H) | 2.98 min 446 (M + H) |
| cyclohexyl | 3.35 min 436 (M + H) | 3.36 min 462 (M + H) | 3.49 min 476 (M + H) |
| benzyl | 3.21 min 444 (M + H) | 3.22 min 470 (M + H) | 3.35 min 484 (M + H) |
| phenethyl | 3.42 min 458 (M + H) | 3.42 min 484 (M + H) | 3.54 min 498 (M + H) |
| cyclohexyl-ethyl | 3.50 min 450 (M + H) | 3.50 min 476 (M + H) | 3.62 min 490 (M + H) |
| styryl | 3.55 min 456 (M + H) | 3.57 min 482 (M + H) | 3.66 min 496 (M + H) |

TABLE 6-continued

LC & MS data for various N-substituted Amides

| R1 | G Guanidine LC & MS | Imidazole LC & MS | THP LC & MS |
|---|---|---|---|
| 2-Cl-phenyl | 3.25 min 464 (M + H) | 3.24 min 490 (M + H) | 3.36 min 504 (M + H) |
| 2-CH3-phenyl | 3.29 min 444 (M + H) | 3.30 min 470 (M + H) | 3.42 min 484 (M + H) |
| 2-OCH3-phenyl | 3.38 min 460 (M + H) | 3.38 min 486 (M + H) | 3.48 min 500 (M + H) |
| 4-Cl-phenyl | 3.58 min 464 (M + H) | 3.59 min 490 (M + H) | 3.70 min 504 (M + H) |
| 4-CH3-phenyl | 3.45 min 444 (M + H) | 3.46 min 470 (M + H) | 3.57 min 484 (M + H) |
| 4-OCH3-phenyl | 3.33 min 460 (M + H) | 3.34 min 486 (M + H) | 3.44 min 500 (M + H) |
| 3-pyridyl | 2.61 min 431 (M + H) | 2.60 min 457 (M + H) | 2.72 min 471 (M + H) |
| 4-pyridyl | 2.58 min 431 (M + H) | 2.57 min 457 (M + H) | 2.70 min 471 (M + H) |
| 2,5-dimethyl-3-furyl | 3.45 min 448 (M + H) | 3.45 min 474 (M + H) | 3.59 min 488 (M + H) |
| 2-Br-phenyl | 3.27 min 509 (M + H) | 3.16 min 534 (M + H) | 3.39 min 548 (M + H) |
| 4-Br-phenyl | 3.65 min 509 (M + H) | 3.28 min 534 (M + H) | 3.76 min 548 (M + H) |
| 2,3-dimethylphenyl | 3.65 min 458 (M + H) | 3.65 min 484 (M + H) | 3.58 min 498 (M + H) |
| 3-Cl-phenyl | 3.46 min 464 (M + H) | 3.56 min 490 (M + H) | 3.70 min 504 (M + H) |

EXAMPLE 22

Parallel Synthesis of 2-Benzyloxycarbonylamino-3-(2-{4-[2-(3-benzylureido)-ethyl]-piperazin-1-yl}acetylamino)-propionic acid

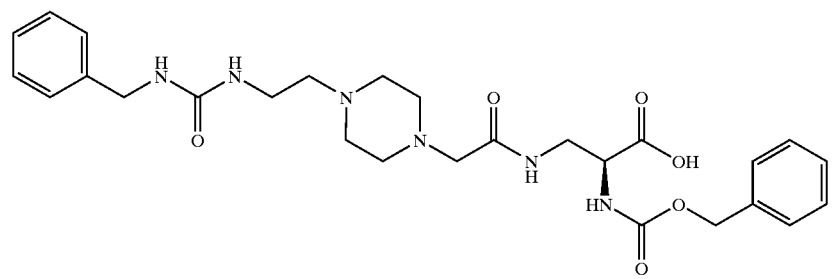

The compound was prepared by following the procedures detailed in examples 1–4, 6,7 and 11, but for example 6, wherein the 4-[(2-fluorenylmethyloxycarbonylamino)-ethoxy]-2-hydroxybenzoic acid was substituted by Fmoc-4-(2-aminoethyl)-1-carboxymethyl-piperazine (Neosystem Lab). The purified product was characterized by MS: 541 (M+H); LC: 3.55 min; 99% @ 220 nm. 1H MNR: (DMSO-d6+D20): d: 7.2–7.5 (m, 10H), 5.1 (s, 2H), 4.3 (s, 2H), 4.2 (q, 1H), 3.6 (m, 1H), 3.45–3.55 (m, 3H), 3.25–3.35 (m, 6H), 3.1 (t, 2H), 2.9 (br, 4H).

EXAMPLE 23

Parallel Synthesis of 2-Benzyloxycarbonylamino-3-(2-{4-[2-(3-benzylureido)-ethyl]-2,4-dioxo-3,4-dihydro-2H-quinazolin-1-yl}acetylamino)-propionic acid

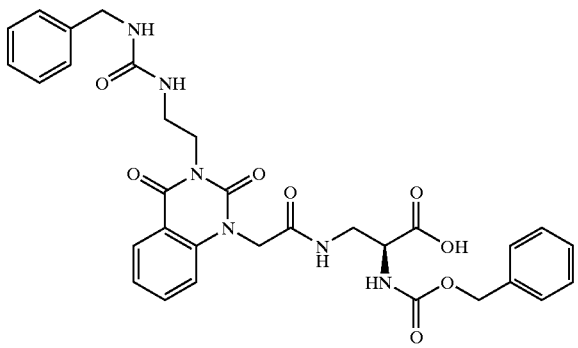

The compound was prepared by following the procedures detailed in examples 1–4, 6,7 and 11, but for example 6, wherein the 4-[(2-fluorenylmethyloxycarbonyl-amino)-ethoxy]-2-hydroxybenzoic acid was substituted by Fmoc-4-(2-aminoethyl)-1-carboxymethyl-quinazoline-2,4-dione (Neosystem Lab). The purified product was characterized by MS: 617 (M+H); LC: 4.41 min; 98% @ 220 nm. 1H MNR: (DMSO-d6+D20): d: 8.05 (dd, 1H), 7.6 (t, 1H), 7.2–7.4 (m, 10H), 7.0 (t, 2H) 5.0 (s, 2H), 4.7 (m, 2H), 3.8–4.0 (m, 4H), 3.45 (m, 1H), 3.25–3.35 (m, 4H).

The compounds of the present invention can be used in the form of salts derived from pharmaceutically or physiologically acceptable acids or bases. These salts include, but are not limited to, salts with inorganic acids such as hydrochloric acid, sulfuric acid, nitric acid, phosphoric acid and salts with organic acids such as acetic acid, oxalic acid, succinic acid, and maleic acid. Other salts include salts with alkali metals or alkaline earth metals, such as sodium, potassium, calcium or magnesium. The compounds of the present invention can also be used in the form of esters at the C-terminus; carbamates, amides and the like at the N-terminus or other conventional ipro-drugi forms which, when administered, convert to the active moiety in vivo.

Compounds of the present invention may be administered in combination with one or more pharmaceutically acceptable carriers, for example, solvents, diluents and the like. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils. Adjuvants customarily employed in the preparation of pharmaceutical compositions may be advantageously included, such as flavoring agents, coloring agents, preserving agents, and antioxidants, for example, vitamin E, ascorbic acid, BHT and BHA. These compounds may be administered orally as well as by intravenous, intramuscular, or subcutaneous routes. When administered orally in such forms as tablets, capsules, dispersible powders, granules, or suspensions, formulations may contain, for example, from about 0.05 to 5% of suspending agent, syrups containing, for example, from about 10 to 50% of sugar, or elixirs containing, for example, from about 20 to 50% ethanol, and the like. When administration is parenterally, formulation may be, for example, sterile injectable solutions or suspensions containing from about 0.05 to 5% suspending agent in an isotonic medium. Such pharmaceutical preparations may contain, for example, from about 25 to about 90% by weight of active ingredient in combination with a carrier, and more preferably between about 5% and 60% by weight of active ingredient.

The preferred pharmaceutical compositions from the standpoint of ease of preparation and administration are solid compositions, particularly tablets and hard-filled or liquid-filled capsules. Oral administration of the compounds is preferred.

The dosage requirements can be determined by one skilled in the art and will vary with the particular composition employed, the route of administration, the severity of the symptoms presented and the particular subject being treated. However, in general, satisfactory results are obtained when compounds of the invention are administered at a daily dosage of from about 0.5 to about 500 mg/kg of animal body weight, preferably given in divided doses two to four times a day, or in a sustained release form. Preferably, the total daily dosage is from about 1 to about 100 mg, preferably about 2 to about 80 mg. Dosage forms suitable for internal use comprise from about 0.5 to 500 mg of active compound in intimate admixture with solid or liquid pharmaceutically acceptable carrier.

We claim:

1. A compound having the formula

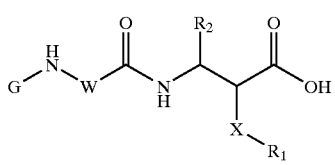

(I)

wherein:

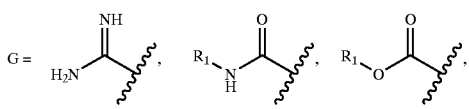

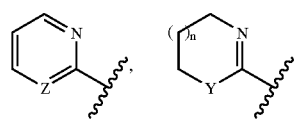

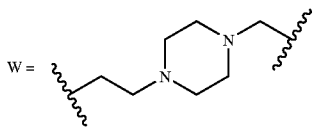

R1 and R2 independently are alkyl of 1–8 carbon atoms, alkenyl of 2–8 carbon atoms, alkynyl of 2–8 carbon atoms, cycloalkyl of 3–12 carbon atoms, aryl, aralkyl of 6 to 10 carbon atoms, heterocycloalkyl of 5–10 members consisting of carbon atoms and from 1 to 3 heteroatoms selected from N, S and O;

R3 is H, alkyl of 1–6 carbon atoms, aralkoxy of 1–6 carbon atoms;

X is NHCOO, NHCO, NHCONH, NHSO2;

Y is CH2, NH;

Z is CH, N, S;

m is 0–4; and n is 0–3; or pharmaceutical salts thereof.

2. A compound of claim 1 wherein R1 is methyl, ethyl, n-propyl, i-propyl, allyl, homoallyl, propargyl, pentyl, neopentyl, n-hexyl, octyl, neopentyl, trichloroethyl, n-butyl, i-butyl, butynyl, phenyl, methylphenyl, dimethylphenyl, halophenyl, methoxyphenyl, acetylphenyl, biphenyl, naphthyl, benzyl, phenethyl, cyclohexyl, cyclohexylmethyl, trimethylcyclopropyl, phenylcyclopropyl, adamantyl, adamantylmethyl, cinnamic, pyridyl, or dimethylfuran.

3. A compound according to claim 1 which is 2-benzyloxycarbonylamino-3-(2-{4-[2-(3-benzylureido)-ethyl]-piperazin-1-yl}acetylamino)-propionic acid or a pharmaceutically acceptable salt thereof.

4. A combinatorial library comprising a plurality of different compounds, each compound covalently linked to a solid support P, according to the formula:

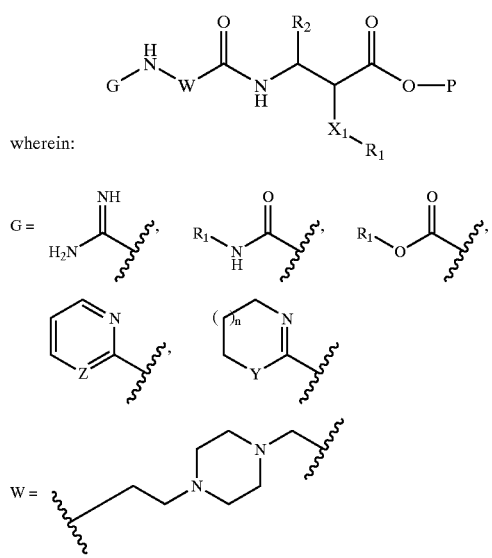

wherein:

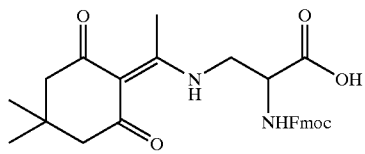

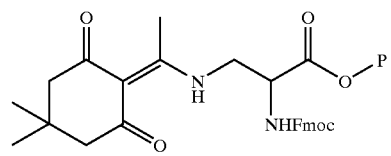

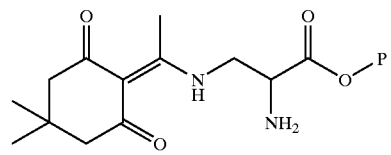

R1 and R2 independently are alkyl of 1–8 carbon atoms, alkenyl of 2–8 carbon atoms, alkynyl of 2–8 carbon atoms, cycloalkyl of 3–12 carbon atoms, aryl, aralkyl of 6 to 10 carbon atoms, heterocycloalkyl of 5–10 members consisting of carbon atoms and from 1 to 3 heteroatoms selected from N, S and O;

R3 is H, alkyl of 1–6 carbon atoms, aralkoxy of 1–6 carbon atoms;

X is NHCOO, NHCO, NHCONH, NHSO2;

Y is CH2, NH;

Z is CH, N, S;

m is 0–4; and n is 0–3; or pharmaceutical salts thereof.

5. A combinatorial library according to claim 4 wherein each of said compounds is prepared by the method which comprises:

a) attaching a β-amino acid of the formula

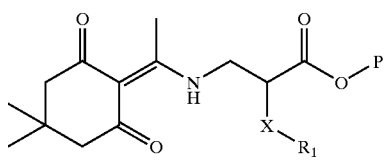

to a solid support P to produce a compound of formula (1)

(1)

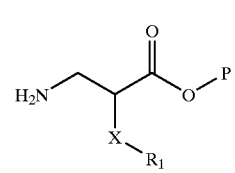

b) deblocking the fluorenylmethyloxy carbonyl group of said compound of formula (1) with piperidine to produce a compound of formula (2)

(2)

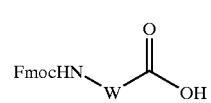

c) acylating said compound of formula (2) with a chemical species selected from chloroformates, isocyanates, sulfonyl chlorides, carboxylic acid chlorides or carboxylic acids to produce a compound of formula (3)

(3)

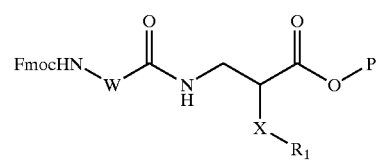

d) deblocking the 4,4-dimethyl-2,6-dioxocylohex-1-ylideneethyl protecting group of said compound of formula (3) with hydrazine to produce a compound of formula (4)

(4)

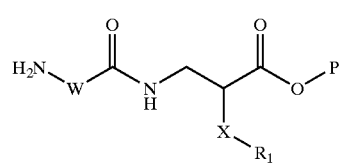

e) reacting said compound of formula (4) with a Fmoc protected amino carboxylic acid of formula (5)

(5)

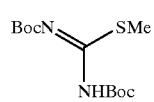

to produce a compound of formula (6)

(6)

f) deblocking the fluorenylmethyloxy carbonyl group of said compound of formula (6) with piperidine to produce a compound of formula (7)

(7)

g) reacting said compound of formula (7) with guanidilation reagents of formula (8) or (9) or (10) or amidation reagent of formula (11)

(8)

-continued

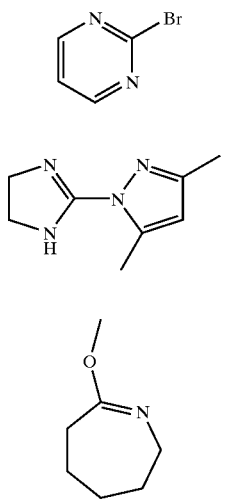

to produce a compound of formula (12)

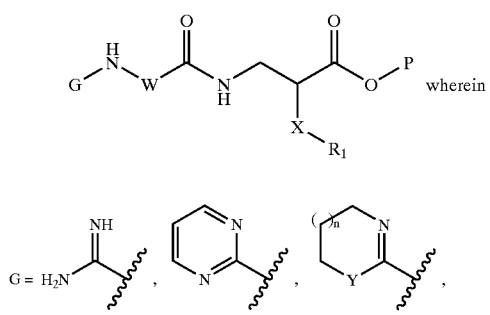

wherein or h) reacting said compound of formula (7) with isocyanates or with p-nitrophenyl chloroformate, followed by amine to produce a compound of formula (12)

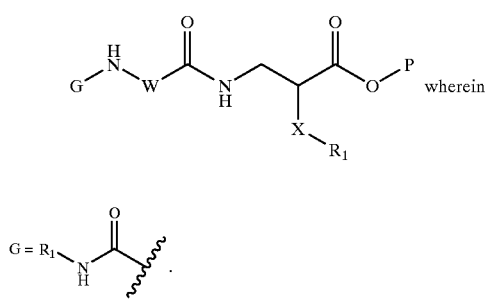

wherein

6. A combinatorial library according to claim 5 wherein the solid support P is polystyrene crosslinked with divinylbenzene and functionalized with a linker such as hydroxymethylphenoxy.

7. A combinatorial library according to claim 4 wherein the solid support P is Wang resin.

8. A method for the solid phase synthesis of compounds of formula (I) of claim 1 or pharmaceutical salts thereof, comprising the steps:

a) attaching a β-amino acid of the formula

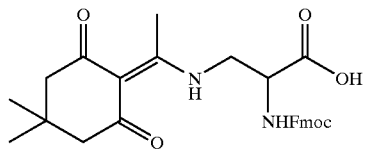

to a solid support P to produce a compound of formula (1)

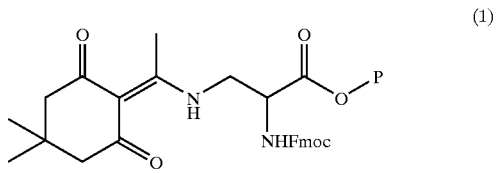

b) deblocking the fluorenylmethyloxy carbonyl group of said compound of formula (1) with piperidine to produce a compound of formula (2)

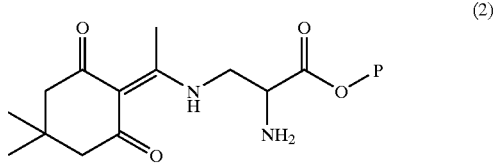

c) acylating said compound of formula (2) with a chemical species selected from chloroformates, isocyanates, sulfonyl chlorides, carboxylic acid chlorides or carboxylic acids to produce a compound of formula (3)

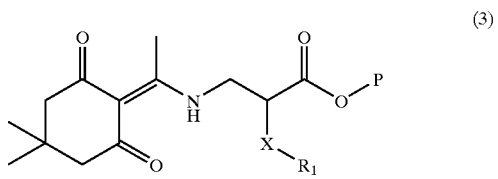

d) deblocking the 4,4-dimethyl-2,6-dioxocylohex-1-ylideneethyl protecting group of said compound of formula (3) with hydrazine to produce a compound of formula (4)

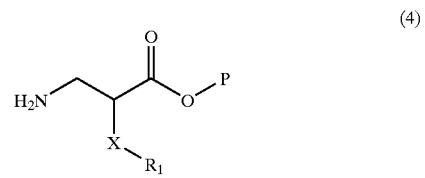

e) reacting said compound of formula (4) with a Fmoc protected amino carboxylic acid of formula (5)

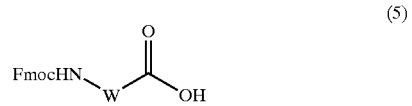

to produce a compound of formula (6)

(6)

FmocHN-W-C(O)-NH-CH₂-CH(X-R₁)-C(O)-O-P f) deblocking the fluorenylmethyloxy carbonyl group of said compound of formula (6) with piperidine to produce a compound of formula (7)

(7)

H₂N-W-C(O)-NH-CH₂-CH(X-R₁)-C(O)-O-P g) reacting said compound of formula (7) with guanidilation reagents of formula (8) or (9) or (10) or amidation reagent of formula (11)

(8)

BocN=C(SMe)NHBoc (9)

2-bromopyrimidine (10)

2-(3,5-dimethylpyrazol-1-yl)-4,5-dihydro-1H-imidazole (11)

7-methoxy-2,3,4,5-tetrahydro-1H-azepine (methoxy cyclic amidine)

to produce a compound of formula (12)

(12)

G-NH-W-C(O)-NH-CH₂-CH(X-R₁)-C(O)-O-P wherein

G = H₂N-C(=NH)-, 2-pyrimidinyl, or cyclic amidine (CH₂)ₙ-Y ring or h) reacting said compound of formula (7) with isocyanates or with p-nitrophenyl chloroformate, followed by amine to produce a compound of formula (12)

(12)

G-NH-W-C(O)-NH-CH₂-CH(X-R₁)-C(O)-O-P wherein

G = R₁-NH-C(O)- i) reacting said compound of formula (12) with a cleaving reagent to produce a compound of formula (I).

9. The method according to claim 8 wherein the solid support used is polystyrene crosslinked with divinylbenzene and functionalized with a linker such as hydroxymethylphenoxy group.

10. The method according to claim 8 wherein the solid support used is Wang resin.

11. The method of claim 8 wherein the cleaving reagent is trifluoroacetic acid.

12. A pharmaceutical composition comprising a compound of claim 1 and at least one pharmaceutically acceptable carrier.

* * * * *

SEQUENCE LISTING

```
<160> NUMBER OF SEQ ID NOS: 9

<210> SEQ ID NO 1
<211> LENGTH: 6
<212> TYPE: PRT
<213> ORGANISM: unknown
<220> FEATURE:
<223> OTHER INFORMATION: synthetic
```

```
<400> SEQUENCE: 1

Gly Arg Gly Asp Ser Pro
1               5

<210> SEQ ID NO 2
<211> LENGTH: 6
<212> TYPE: PRT
<213> ORGANISM: unknown
<220> FEATURE:
<223> OTHER INFORMATION: synthetic

<400> SEQUENCE: 2

Gly Arg Gly Asp Thr Pro
1               5

<210> SEQ ID NO 3
<211> LENGTH: 5
<212> TYPE: PRT
<213> ORGANISM: unknown
<220> FEATURE:
<223> OTHER INFORMATION: synthetic

<400> SEQUENCE: 3

Gly Arg Gly Asp Ser
1               5

<210> SEQ ID NO 4
<211> LENGTH: 4
<212> TYPE: PRT
<213> ORGANISM: unknown
<220> FEATURE:
<223> OTHER INFORMATION: synthetic

<400> SEQUENCE: 4

Arg Gly Asp Ser
1

<210> SEQ ID NO 5
<211> LENGTH: 6
<212> TYPE: PRT
<213> ORGANISM: unknown
<220> FEATURE:
<223> OTHER INFORMATION: synthetic

<400> SEQUENCE: 5

Gly Arg Gly Asp Asn Pro
1               5

<210> SEQ ID NO 6
<211> LENGTH: 6
<212> TYPE: PRT
<213> ORGANISM: unknown
<220> FEATURE:
<223> OTHER INFORMATION: synthetic

<400> SEQUENCE: 6

Gly Arg Gly Glu Ser Pro
1               5

<210> SEQ ID NO 7
<211> LENGTH: 10
<212> TYPE: PRT
<213> ORGANISM: unknown
<220> FEATURE:
<223> OTHER INFORMATION: synthetic
<221> NAME/KEY: MISC_FEATURE
```

```
<222> LOCATION: (2)..(2)
<223> OTHER INFORMATION: penicillamine

<400> SEQUENCE: 7

Gly Xaa Gly Arg Gly Asp Ser Pro Cys Ala
1               5                   10

<210> SEQ ID NO 8
<211> LENGTH: 6
<212> TYPE: PRT
<213> ORGANISM: unknown
<220> FEATURE:
<223> OTHER INFORMATION: synthetic
<221> NAME/KEY: MOD_RES
<222> LOCATION: (1)..(1)
<223> OTHER INFORMATION: METHYLATION

<400> SEQUENCE: 8

Gly Arg Gly Asp Ser Pro
1               5

<210> SEQ ID NO 9
<211> LENGTH: 6
<212> TYPE: PRT
<213> ORGANISM: unknown
<220> FEATURE:
<223> OTHER INFORMATION: synthetic
<221> NAME/KEY: MISC_FEATURE
<222> LOCATION: (1)..(1)
<223> OTHER INFORMATION: D-amino acid

<400> SEQUENCE: 9

Gly Arg Gly Asp Ser Pro
1               5
```